United States Patent
Jo et al.

(10) Patent No.: US 6,552,069 B1
(45) Date of Patent: Apr. 22, 2003

(54) 3-METHYL-CHROMAN AND -THIOCHROMAN DERIVATIVES

(75) Inventors: JaeChon Jo, Seoul (KR); YoungJun Na, Kyonggi-do (KR); HongIl Heo, Kyonggi-do (KR); JongMin Kim, Kyonggi-do (KR); Kazumi Morikawa, Shizuoka (JP); Yoshitake Kanbe, Shizuoka (JP); Masahiro Nishimoto, Shizuoka (JP); MyungHwa Kim, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/149,751

(22) PCT Filed: Dec. 13, 2000

(86) PCT No.: PCT/JP00/08808

§ 371 (c)(1),
(2), (4) Date: Jun. 13, 2002

(87) PCT Pub. No.: WO01/42234

PCT Pub. Date: Jun. 14, 2001

(30) Foreign Application Priority Data

Dec. 13, 1999 (JP) ............................................ 11-353436

(51) Int. Cl.[7] ...................... A61K 31/38; A61K 31/35; C07D 335/04; C07D 311/04
(52) U.S. Cl. .................. 514/432; 514/456; 549/23; 549/406
(58) Field of Search ................... 549/23, 406; 514/432, 514/456

(56) References Cited

U.S. PATENT DOCUMENTS 6,153,768 A * 11/2000 Jo et al. ..................... 549/406
6,313,160 B1 * 11/2001 Guillaumet et al. ......... 514/430
6,316,494 B1 * 11/2001 Jacobsen et al. ............ 514/456
6,479,670 B1 * 11/2002 Belloni et al. .................. 549/9

* cited by examiner

Primary Examiner—Deborah C. Lambkin
(74) Attorney, Agent, or Firm—Browdy and Neimark, P.L.L.C.

(57) ABSTRACT

The present invention provides a compound having the following general formula (1):

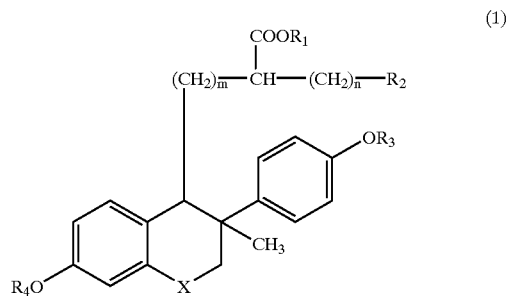

in which
$R_1$ represents a hydrogen atom, etc.;
$R_2$ represents a $C_3$–$C_3$ perhalogenoalkyl group, etc.;
each of $R_3$ and $R_4$ independently represents a hydrogen atom, etc.;
X represents an oxygen atom or a sulfur atom;
m represents an integer of 2 to 14; and
n represents an integer of 0 to 8;

or enantiomers of the compound, or hydrates or pharmaceutically acceptable salts of the compound or its enantiomers. The compound of general formula (1) is advantageous in pharmaceutical use because of its anti-estrogenic activity.

18 Claims, No Drawings

3-METHYL-CHROMAN AND -THIOCHROMAN DERIVATIVES

This application is a 371 of PCT/JP00/08808 Dec. 13, 2000.

TECHNICAL FIELD

The present invention relates to chroman or thiochroman derivatives having anti-estrogenic activity.

BACKGROUND ART

In treating diseases caused by abnormal tissue growth that is dependent upon a certain sexual steroidal hormone such as estrogen, it is highly important to significantly inhibit, more preferably completely eliminate, the effect induced by the hormone. For this purpose, it is desirable to reduce the level of hormone capable of acting on the steroidal hormone receptor site. For instance, anti-estrogenic agents are commonly administered for alternative or combination therapy to limit the production of estrogen to the amount less than required to activate the receptor site. However, such conventional technique for blocking estrogen production could not sufficiently inhibit the effect induced through the estrogen receptor. Practically, even when estrogen is completely absent, some of the receptors may be activated. It was therefore considered that estrogen antagonists could provide better therapeutic effect in comparison to the technique for blocking only the production of sexual steroidal hormone. Thus, numerous estrogen antagonists have been developed. For example, many patent publications including U.S. Pat. Nos. 4,760,061, 4,732,912, 4,904,661, 5,395,842 and WO 96/22092 disclose various anti-estrogenic compounds. Sometimes, however, prior art antagonists may themselves act as agonists, and therefore activate rather than block the receptor. For example, Tamoxifen has been most widely used as an anti-estrogenic agent. However, this agent has a disadvantage that it exhibits estrogenic activity in some organs (see, M. Harper and A. Walpole, J. Reprod. Fertile., 1967, 13, 101).

As another non-steroidal anti-estrogenic compound, WO 93/10741 discloses a benzopyran derivative having an aminoethoxyphenyl substituent(s) (Endorecherche), the typical compound of which is EM-343 having the following structure:

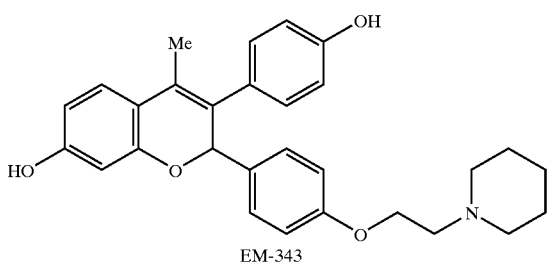

EM-343

Said compound also has the agonistic effect. It is therefore required to develop an anti-estrogenic compound which is substantially or completely free of agonistic effect and which can effectively block the estrogen receptor.

In addition, it has been known that 7α-substituted derivatives of estradiol, for example, 7α-$(CH_2)_{10}$CONMeBu derivatives, are steroidal anti-estrogenic agents without agonistic effect (see, EP-A 0138504, U.S. Pat. No. 4,659,516). Further, an estradiol derivative having a 7α-$(CH_2)_9SOC_5H_6F_5$ substituent has also been disclosed (see, Wakeling et al., Cancer Res., 1991, 51, 3867).

Non-steroidal anti-estrogenic agents without agonistic effect have been first reported by Wakeling et al. in 1987 (see, A. Wakeling and Bowler, J. Endocrinol., 1987, 112, R7). Meanwhile, U.S. Pat. No. 4,904,661 discloses phenol derivatives having anti-estrogenic activity. These phenol derivatives generally have a naphthalene scaffold and include, typically, the following compounds:

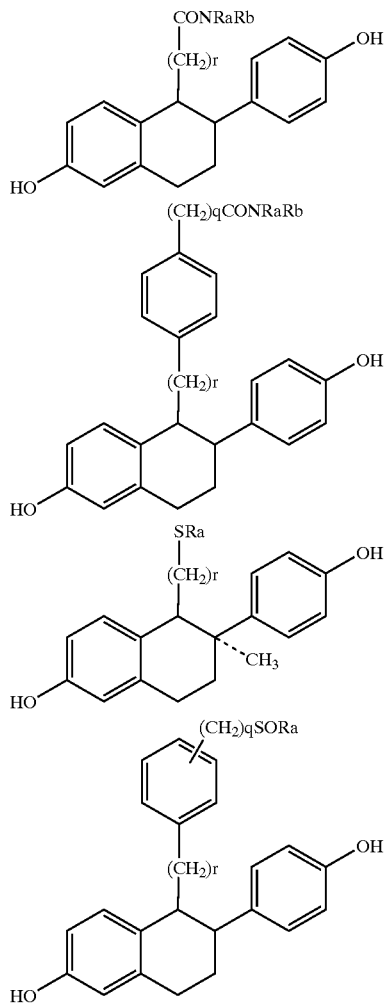

Some chroman and thiochroman derivatives have been reported as anti-estrogenic compounds having no agonistic effect (WO 98/25916). Although the existing anti-estrogenic compounds having no agonistic effect show a substantial therapeutic effect when administered via intravenous or subcutaneous injection, they show a highly reduced therapeutic effect when administered orally, probably due to their low bioavailability by oral route, etc. Therefore, for convenience's sake in the case of administration, it is desired to develop anti-estrogenic compounds which show a sufficient effect when administered orally and at the same time have no agonistic effect.

DISCLOSURE OF THE INVENTION

The object of the present invention is to provide chroman or thiochroman derivatives which have anti-estrogenic activity and are advantageous in pharmaceutical use.

The present inventors researched anti-estrogenic activity of compounds having various structures. As a result, we have found that chroman or thiochroman derivatives of general formula (1) could show a good anti-estrogenic activity in substantial absence of agonistic effect and that they provided a sufficiently high activity even when administered orally. The present invention has been accomplished on the basis of this finding.

Namely, the present invention provides a compound having the following general formula (1):

$$\text{(1)}$$

[Structure showing a chromane/thiochromane core with substituents: COOR$_1$ on (CH$_2$)$_m$—CH—(CH$_2$)$_n$—R$_2$ chain, OR$_3$ on phenyl ring, CH$_3$ on ring carbon, R$_4$O on fused benzene ring, and X in the ring]

in which
R$_1$ represents a hydrogen atom or a salt-forming metal;
R$_2$ represents a linear or branched C$_3$–C$_5$perhalogenoalkyl group or a group of the following general formula (2):

$$\text{(2)}$$

[Structure showing a branching point with R$_5$ and R$_6$ substituents]

in which
each of R$_5$ and R$_6$ represents a linear or branched C$_1$–C$_3$ perhalogenoalkyl group;
each of R$_3$ and R$_4$ independently represents a hydrogen atom, an optionally substituted linear or branched C$_1$–C$_3$ alkyl group, an acyl group or a salt-forming metal;
X represents an oxygen atom or a sulfur atom;
m represents an integer of 2 to 14; and
n represents an integer of 0 to 8;
or enantiomers of the compound, or hydrates or pharmaceutically acceptable salts of the compound or its enantiomers.

In addition, the present invention provides a pharmaceutical composition comprising a compound of general formula (1) as an active ingredient. Further, the present invention provides an anti-estrogenic pharmaceutical composition comprising the above compound as an active ingredient. The present invention also provides a therapeutic agent for breast cancer comprising the above compound as an active ingredient.

Salt-forming metals as R$_1$ include, but are not limited to, alkali metals such as sodium and potassium, alkaline earth metals such as magnesium and calcium, rare earth metals such as cerium and samarium, as well as zinc and tin. Among these, preferred are alkali metals and alkaline earth metals, particularly sodium, potassium and calcium.

R$_1$ may preferably be a hydrogen atom, an alkali metal or an alkaline earth metal.

Halogens in the linear or branched C$_3$–C$_5$ perhalogenoalkyl groups as R$_2$ include fluorine, chlorine, bromine and iodine, with fluorine being preferred. Alkyls in the linear or branched C$_3$–C$_5$ perhalogenoalkyl groups under consideration include, n-propyl, i-propyl, n-butyl, i-butyl, sec-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl and 1-ethylpropyl. Preferred are linear or branched C$_3$–C$_4$ alkyls, e.g., n-propyl and n-butyl.

Examples of the linear or branched C$_3$–C$_5$ perhalogenoalkyl group as R$_2$ include the above-listed linear or branched C$_3$–C$_5$ alkyl groups, provided that they are perhalogenated, preferably perfluorinated, for example, perfluoro-n-propyl, perfluoro-n-butyl and perfluoro-n-pentyl. More specifically, a perfluoro-n-butyl group is preferred.

In the case where R$_2$ is a group of general formula (2), halogens in the linear or branched C$_1$–C$_3$ perhalogenoalkyl groups as R$_5$ and R$_6$ include fluorine, chlorine, bromine and iodine, with fluorine being preferred. Alkyls in the linear or branched C$_1$–C$_3$ perhalogenoalkyl groups under consideration include, methyl, ethyl, n-propyl and i-propyl, with methyl being preferred.

In the case where R$_2$ is a group of general formula (2), examples of the linear or branched C$_1$–C$_3$ perhalogenoalkyl group as R$_5$ and R$_6$ include the above-listed linear or branched C$_1$–C$_3$ alkyl groups, provided that they are perhalogenated, preferably perfluorinated. Further, perhalogenated C$_1$ alkyl groups are preferred and a perfluorinated group is particularly preferred. More specifically, a perfluoromethyl group is preferred.

A group of general formula (2) as R$_2$ is preferably a 1,1,1,3,3,3-hexafluoroisopropyl group.

Having the definition given above, R$_2$ is preferably a perfluoro-n-butyl group.

Alkyls in the optionally substituted linear or branched C$_1$–C$_3$ alkyl groups as R$_3$ and R$_4$ include, but are not limited to, methyl, ethyl, n-propyl and i-propyl.

Substituents on the optionally substituted linear or branched C$_1$–C$_3$ alkyl groups as R$_3$ and R$_4$ include, an alkoxy group having a linear or branched C$_1$–C$_5$ alkyl as its alkyl moiety and a hydroxyl group, more specifically a methoxy group.

Examples of the optionally substituted linear or branched C$_1$–C$_3$ alkyl group as R$_3$ and R$_4$ include the above-listed alkyl groups, provided that they may be substituted with the above-listed substituents. Specific examples of the substituted alkyl group include a methoxymethyl group.

Examples of the acyl group as R$_3$ and R$_4$ include, an acetyl group, a benzoyl group and a pivaloyl group.

Salt-forming metals as R$_3$ and R$_4$ include, independently, alkali metals such as sodium and potassium, alkaline earth metals such as magnesium and calcium, rare earth metals such as cerium and samarium, as well as zinc and tin. Among these, preferred are alkali metals and alkaline earth metals, particularly sodium, potassium and calcium.

Preferably, R$_3$ and R$_4$ are independently a hydrogen atom or a salt-forming metal.

In a suitable combination of R$_1$, R$_3$ and R$_4$, at least one or all of them may be a hydrogen atom and the remainder may be a salt-forming metal. Examples of such combination include the following: a combination where R$_1$, R$_3$ and R$_4$ are each a hydrogen atom; a combination where R$_1$ is a salt-forming metal (e.g., an alkali metal such as sodium) and R$_3$ and R$_4$ are each a hydrogen atom; and a combination where R$_1$, R$_3$ and R$_4$ are each a salt-forming metal (e.g., an alkali metal such as sodium).

X may preferably be an oxygen atom or a sulfur atom.

m may preferably be an integer of 6 to 10, particularly 8 or 9.

n may preferably be an integer of 0 to 8, particularly 2 to 4.

Compounds of general formula (1) have enantiomers. All individual enantiomers and mixtures thereof are intended to be within the scope of the present invention. Among the enantiomers, preferred are compounds where the configuration of 3- and 4-position chiral carbons in the parent scaffold (i.e., chroman or thiochroman ring) in general formula (1) is (3RS,4RS), (3R,4R) or (3S,4S). Also compounds having R- or S-configuration at the carbon to which the carboxylic acid or its metal salt is bonded, wherein said carbon is the carbon on the side chain which is bonded to 4-position of the parent scaffold (i.e., chroman or thiochroman ring) and mixtures of such compounds at any ratio are preferable.

Among compounds of general formula (1), preferred are those compounds in which $R_1$ is a hydrogen atom, an alkali metal or an alkaline earth metal; $R_2$ is a perfluoro-n-propyl group, a perfluoro-n-butyl group or a 1,1,1,3,3,3-hexafluoroisopropyl group; each of $R_3$ and $R_4$ is independently a hydrogen atom, an alkali metal or an alkaline earth metal; X is an oxygen atom or a sulfur atom; m is an integer of 8 or 9; and n is an integer of 2 to 4. Particularly preferred are compounds in which:

a) $R_1$ is a hydrogen atom, $R_2$ is a perfluoro-n-butyl group, $R_3$ is a hydrogen atom, $R_4$ is a hydrogen atom, X is a sulfur atom, m is 8, and n is 2;

b) $R_1$ is a hydrogen atom, $R_2$ is a perfluoro-n-butyl group, $R_3$ is a hydrogen atom, $R_4$ is a hydrogen atom, X is a sulfur atom, m is 8, and n is 3;

c) $R_1$ is a hydrogen atom, $R_2$ is a perfluoro-n-butyl group, $R_3$ is a hydrogen atom, $R_4$ is a hydrogen atom, X is a sulfur atom, m is 8, and n is 4;

d) $R_1$ is a hydrogen atom, $R_2$ is a perfluoro-n-butyl group, $R_3$ is a hydrogen atom, $R_4$ is a hydrogen atom, X is a sulfur atom, m is 9, and n is 2;

e) $R_1$ is a hydrogen atom, $R_2$ is a perfluoro-n-butyl group, $R_3$ is a hydrogen atom, $R_4$ is a hydrogen atom, X is a sulfur atom, m is 9, and n is 3;

f) $R_1$ is a hydrogen atom, $R_2$ is a perfluoro-n-butyl group, $R_3$ is a hydrogen atom, $R_4$ is a hydrogen atom, X is an oxygen atom, m is 8, and n is 2;

g) $R_1$ is a hydrogen atom, $R_2$ is a perfluoro-n-butyl group, $R_3$ is a hydrogen atom, $R_4$ is a hydrogen atom, X is an oxygen atom, m is 9, and n is 2;

h) $R_1$ is a hydrogen atom, $R_2$ is a perfluoro-n-butyl group, $R_3$ is a hydrogen atom, $R_4$ is a hydrogen atom, X is an oxygen atom, m is 8, and n is 3;

i) $R_1$ is a hydrogen atom, $R_2$ is a perfluoro-n-butyl group, $R_3$ is a hydrogen atom, $R_4$ is a hydrogen atom, X is an oxygen atom, m is 9, and n is 3;

j) $R_1$ is a sodium atom, $R_2$ is a perfluoro-n-butyl group, $R_3$ is a hydrogen atom, $R_4$ is a hydrogen atom, X is a sulfur atom, m is 8, and n is 2; or k) $R_1$ is a sodium atom, $R_2$ is a perfluoro-n-butyl group, $R_3$ is a hydrogen atom, $R_4$ is a hydrogen atom, X is an oxygen atom, m is 9, and n is 2.

The compounds of the present invention may be obtained as hydrates.

As typical examples of these compounds, the following compounds can be mentioned:

10-[(3RS,4RS)-7-hydroxy-3-(4-hydroxyphenyl)-3-methyl-thiochroman-4-yl]-2-(3,3,4,4,5,5,6,6,6-nonafluorohexyl) decanoic acid;

10-[(3RS,4RS)-7-hydroxy-3-(4-hydroxyphenyl)-3-methyl-thiochroman-4-yl]-2-(4,4,5,5,6,6,7,7,7-nonafluoroheptyl) decanoic acid;

10-[(3RS,4RS)-7-hydroxy-3-(4-hydroxyphenyl)-3-methyl-thiochroman-4-yl]-2-(5,5,6,6,7,7,8,8,8-nonafluorooctyl) decanoic acid;

11-[(3RS,4RS)-7-hydroxy-3-(4-hydroxyphenyl)-3-methyl-thiochroman-4-yl]-2-(3,3,4,4,5,5,6,6,6-nonafluorohexyl) undecanoic acid;

11-[(3RS,4RS)-7-hydroxy-3-(4-hydroxyphenyl)-3-methyl-thiochroman-4-yl]-2-(4,4,5,5,6,6,7,7,7-nonafluoroheptyl) undecanoic acid;

10-[(3RS,4RS)-7-hydroxy-3-(4-hydroxyphenyl)-3-methyl-chroman-4-yl]-2-(3,3,4,4,5,5,6,6,6-nonafluorohexyl) decanoic acid;

11-[(3RS,4RS)-7-hydroxy-3-(4-hydroxyphenyl)-3-methyl-chroman-4-yl]-2-(3,3,4,4,5,5,6,6,6-nonafluorohexyl) undecanoic acid;

10-[(3RS,4RS)-7-hydroxy-3-(4-hydroxyphenyl)-3-methyl-chroman-4-yl]-2-(4,4,5,5,6,6,7,7,7-nonafluoroheptyl) decanoic acid;

11-[(3RS,4RS)-7-hydroxy-3-(4-hydroxyphenyl)-3-methyl-chroman-4-yl]-2-(4,4,5,5,6,6,7,7,7-nonafluoroheptyl) undecanoic acid;

sodium 10-[(3RS,4RS)-7-hydroxy-3-(4-hydroxyphenyl)-3-methylthiochroman-4-yl]-2-(3,3,4,4,5,5,6,6,6-nonafluorohexyl)decanoate; and sodium 11-[(3RS,4RS)-7-hydroxy-3-(4-hydroxyphenyl)-3-methylchroman-4-yl]-2-(3,3,4,4,5,5,6,6,6-nonafluorohexyl)undecanoate.

As an optically active compound of general formula (1) that has chiral carbons at positions 3 and 4 of the parent scaffold and at α-position to the carboxyl group of the side chain, each of the compounds represented by Peaks 1 and 2 in Examples 19, 21, 24 and 26 stated below is preferred.

Pharmaceutically acceptable salts include, the above-mentioned metal salts, for example, sodium, potassium and calcium salts. Such metal salts may be formed with a carboxyl group and/or a phenolic hydroxyl group in the compound of the present invention.

The compound of general formula (1) may be administered as a pharmaceutical composition in any dosage form suitable for the intended route of administration, in combination with one or more pharmaceutically acceptable diluents, wetting agents, emulsifiers, dispersants, auxiliary agents, preservatives, buffers, binders, stabilizers and the like. The compound and composition may be administered parenterally or orally.

The dose of the compound can be suitably determined according to the physique, age and physical condition of a patient, severity of the disease to be treated, elapsed time after onset of the disease, etc. For example, the compound is generally used in an amount of 0.1 to 500 mg/day when orally administered and in an amount of 1 to 1000 mg/month when parenterally administered (by intravenous, intramuscular, or subcutaneous route) for adult patient.

BEST MODE FOR CARRYING OUT THE INVENTION

The compound of general formula (1) can be prepared according to any one of the following Reaction Schemes 1 to 10 (Processes 1 to 10).

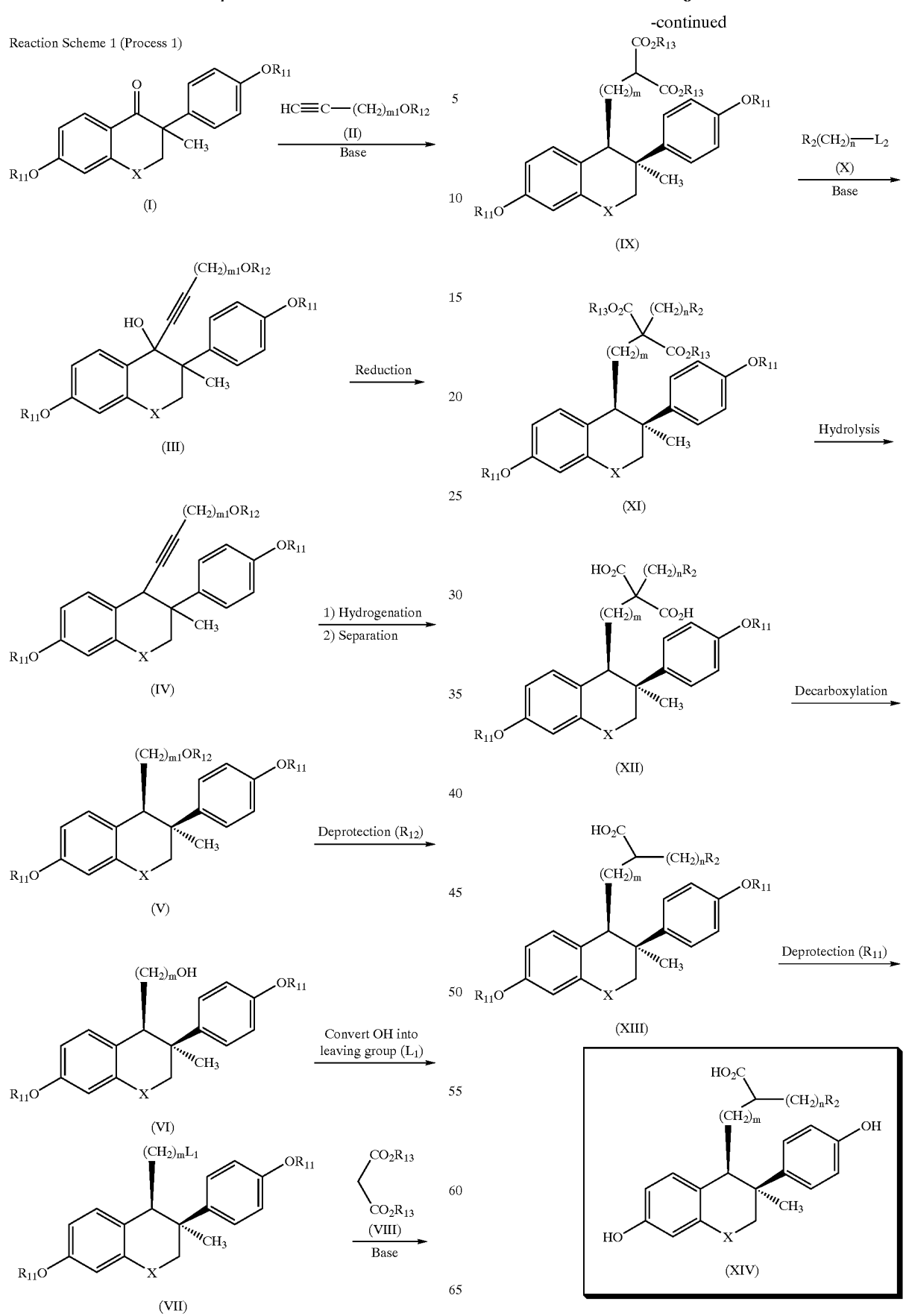

In the above Reaction Scheme 1 (Process 1), $R_2$, X, m and n are as defined above in general formula (1); each of $R_{11}$, $R_{12}$ and $R_{13}$ represents a protecting group; each of $L_1$ and $L_2$ represents a leaving group; and $m_1$ equals m-2.

Reaction Scheme 2 (Process 2)

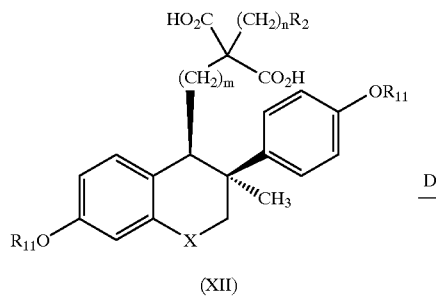

(XII)

Deprotection ($R_{11}$)

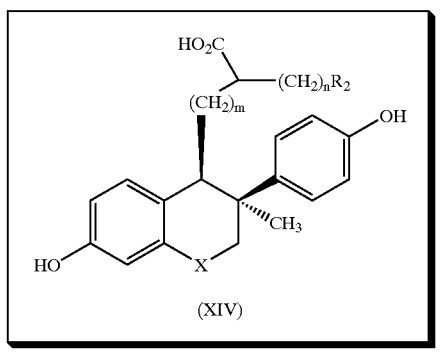

(XV)

Decarboxylation

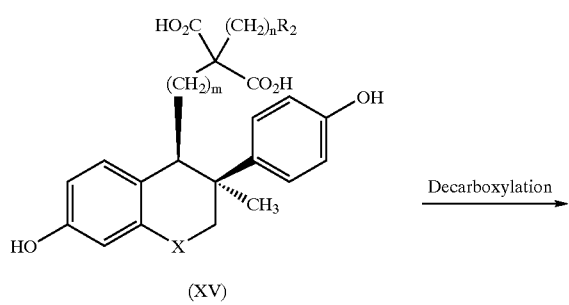

(XIV)

In the above Reaction Scheme 2 (Process 2), $R_2$, X, m and n are as defined above in general formula (1); and $R_{11}$ represents a protecting group.

Reaction Scheme 3 (Process 3)

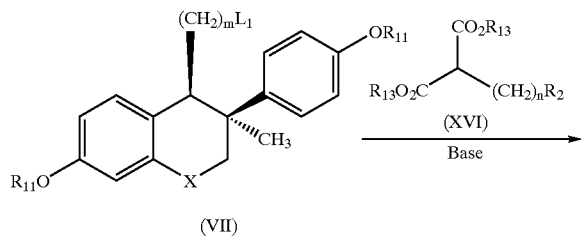

(VII)

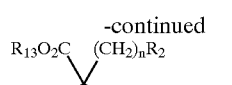

(XI)

Anaolgous procedure to Process 1 or 2

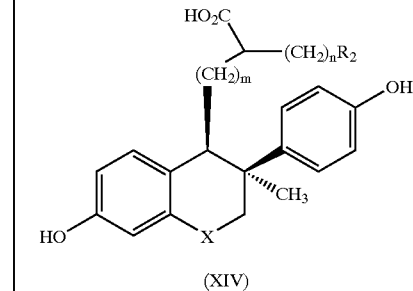

(XIV)

In the above Reaction Scheme 3 (Process 3), $R_2$, X, m and n are as defined above in general formula (1); each of $R_{11}$ and $R_{13}$ represents a protecting group; and $L_1$ represents a leaving group.

Reaction Scheme 4 (Process 4)

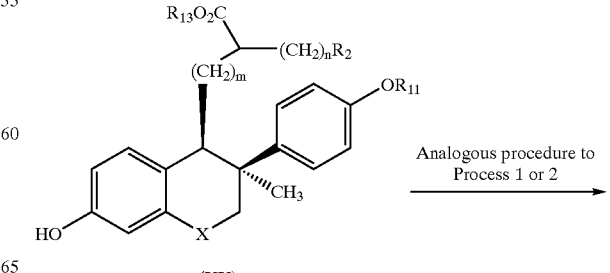

(XVII)

Metathesis (XIX)

Hydrogenation

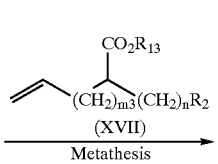

(XX)

Analogous procedure to Process 1 or 2

-continued

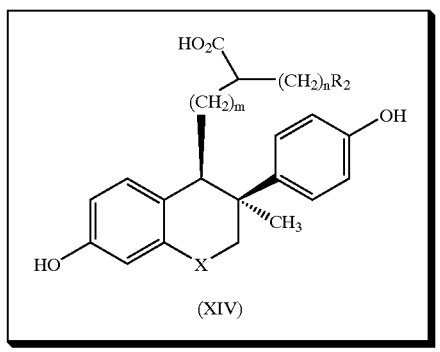

(XIV)

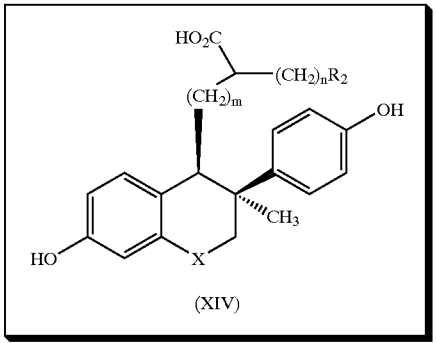

(XIV)

In the above Reaction Scheme 4 (Process 4), $R_2$, X, m and n are as defined above in general formula (1); each of $R_{11}$ and $R_{13}$ represents a protecting group; and $m_3+3$ equals m.

Reaction Scheme 5 (Process 5)

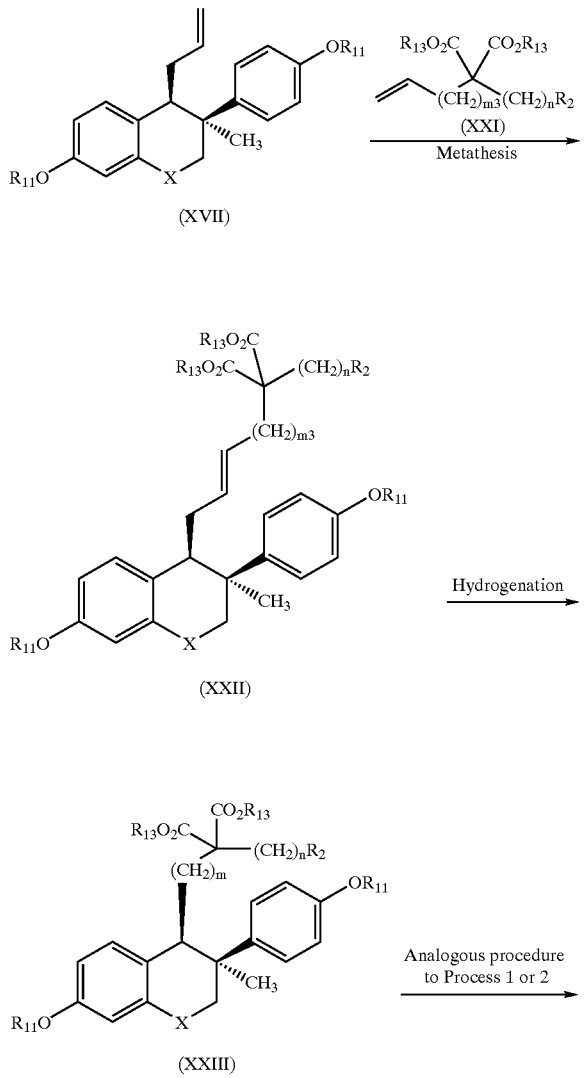

In the above Reaction Scheme 5 (Process 5), $R_2$, X, m and n are as defined above in general formula (1); each of $R_{11}$ and $R_{13}$ represents a protecting group; and $m_3+3$ equals m.

The preparation of the compounds according to the present invention will be illustrated below in more detail, in line with the above-mentioned reaction schemes.

[Process 1]

In the presence of a base (e.g., n-butyllithium, s-butyllithium, sodium hydride), compound (I) is reacted with alkyne (II) in an inert solvent (e.g., tetrahydrofuran, diethyl ether, dioxane, dichloromethane, chloroform, preferably tetrahydrofuran or dioxane) at a temperature ranging from −78° C. to the boiling point of the reaction mixture, preferably from −78° C. to room temperature, to give compound (III).

In the presence of a Lewis acid such as zinc iodide, compound (III) is reduced with sodium cyanoborohydride ($NaBH_3CN$) in an inert solvent (e.g., tetrahydrofuran, diethyl ether, dioxane, dichloromethane, dichloroethane or chloroform, preferably dichloroethane) at a temperature ranging from −78° C. to the boiling point of the reaction mixture, preferably from 0° C. to room temperature, to give compound (IV).

Using a catalyst (e.g., palladium on activated carbon, palladium hydroxide, platinum oxide), compound (IV) is hydrogenated in an inert solvent (e.g., methanol, ethanol, ethyl acetate, tetrahydrofuran, dioxane, preferably tetrahydrofuran, ethyl acetate) at a temperature ranging from room temperature to the boiling point of the reaction mixture, preferably at room temperature, to give compound (V). Compound (V) can be directly prepared from compound (III) through hydrogenation using a catalyst (e.g., palladium on activated carbon, palladium hydroxide or platinum oxide) in an inert solvent (e.g., methanol, ethanol, ethyl acetate, tetrahydrofuran, dioxane, preferably tetrahydrofuran, ethyl acetate) at a temperature ranging from room temperature to the boiling point of the reaction mixture, preferably at room temperature.

Compound (V) is subjected to deprotection of the alcoholic hydroxyl group in an inert solvent to give compound (VI).

In the presence of a base (e.g., triethylamine or pyridine), compound (VI) is treated with methanesulfonyl chloride or p-toluenesulfonyl chloride in an inert solvent (e.g., tetrahydrofuran, dioxane, dichloromethane, dichloroethane or chloroform, preferably dichloromethane) at a temperature ranging from room temperature to the boiling point of the reaction mixture, preferably at room temperature, to convert $(CH_2)_mOH$ in compound (VI) into $(CH_2)_m$—O—$SO_2CH_3$ or $(CH_2)_m$—$SO_2$—$C_6H_4$—p—$CH_3$. The compound thus obtained is then treated with a metal halide (e.g., sodium iodide or potassium iodide) in an inert solvent (e.g., acetone, tetrahydrofuran, dioxane, dichloromethane, dichloroethane or chloroform, preferably acetone) at a temperature ranging from room temperature to the boiling point of the reaction mixture, preferably at the boiling point of the reaction mixture, to give compound (VII).

In the presence of a base (e.g., sodium hydride, sodium hydroxide or potassium t-butoxide), compound (VII) is reacted with a malonic ester of formula (VIII) (e.g., diethyl malonate or dimethyl malonate) in an inert solvent (e.g., tetrahydrofuran, dioxane, dimethylformamide, dichloromethane, dichloroethane or chloroform, preferably tetrahydrofuran) at a temperature ranging from room temperature to the boiling point of the reaction mixture to give compound (IX).

In the presence of a base (e.g., sodium hydride, sodium hydroxide or potassium t-butoxide), compound (IX) is reacted with an alkylating agent of formula (X) in an inert solvent (e.g., tetrahydrofuran, diethyl ether, dioxane, dimethylformamide, dichloromethane, dichloroethane or chloroform, preferably tetrahydrofuran) at a temperature ranging from room temperature to the boiling point of the reaction mixture to give compound (XI).

Compound (XI) is treated with sodium hydroxide or potassium hydroxide in a solvent (e.g., water, ethanol, methanol, a water/ethanol mixture or a water/methanol mixture) at a temperature ranging from room temperature to the boiling point of the reaction mixture, preferably at the boiling point of the reaction mixture, to give compound (XII).

In a solvent (e.g., dimethyl sulfoxide, dimethylformamide, benzene, toluene, xylene, dioxane or tetrahydrofuran) and, if necessary, in the presence of an acid (e.g., hydrogen chloride, sulfuric acid or p-toluenesulfonic acid), compound (XII) is heated to a temperature ranging from 50° C. to the boiling point of the reaction mixture to give compound (XIII).

Next, compound (XIII) is subjected to deprotection of the phenolic hydroxyl group to give compound (XIV).

[Process 2]

Compound (XIV) may also be synthesized from compound (XII) in the following manner. A procedure analogous to Process 1 is repeated until compound (XII) is prepared.

Compound (XII) is subjected to deprotection of the phenolic hydroxyl group to give compound (XV).

In a solvent (e.g., dimethyl sulfoxide, dimethylformamide, benzene, toluene, xylene, dioxane or tetrahydrofuran) and, if necessary, in the presence of an acid (e.g., hydrogen chloride, sulfuric acid or p-toluenesulfonic acid), compound (XV) is heated to a temperature ranging from 50° C. to the boiling point of the reaction mixture to give compound (XIV).

[Process 3]

Compound (XIV) can also be prepared from compound (VII) in the following manner.

In the presence of a base (e.g., sodium hydride, sodium hydroxide or potassium t-butoxide), compound (VII) is reacted with compound (XVI) in an inert solvent (e.g., tetrahydrofuran, dioxane, dimethylformamide, dichloromethane, dichloroethane or chloroform, preferably tetrahydrofuran) at a temperature ranging from −78° C. to the boiling point of the reaction mixture to give compound (XI).

Compound (XI) is converted into compound (XIV) as in Process 1 or 2.

[Process 4]

Compound (XIV) may also be prepared in the following manner.

In the presence of a catalyst such as benzylidene-bis(tricyclohexylphosphine)dichlororuthenium, compound (XVII) is reacted with compound (XVIII) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (XIX).

Using a catalyst (e.g., palladium on activated carbon, palladium hydroxide, platinum oxide or Wilkinson's catalyst), compound (XIX) is hydrogenated in an inert solvent (e.g., methanol, ethanol, ethyl acetate, tetrahydrofuran, dioxane or benzene) at a temperature ranging from room temperature to the boiling point of the reaction mixture, preferably at room temperature, to give compound (XX).

Compound (XX) is converted into compound (XIV) as in Process 1 or 2 where compound (XI) is converted into compound (XIV).

[Process 5]

Further, compound (XIV) may also be prepared in the following manner.

In the presence of a catalyst such as benzylidene-bis(tricyclohexylphosphine)dichlororuthenium, compound (XVII) is reacted with compound (XXI) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (XXII).

Using a catalyst (e.g., palladium on activated carbon, palladium hydroxide, platinum oxide or Wilkinson's catalyst), compound (XXII) is hydrogenated in an inert solvent (e.g., methanol, ethanol, ethyl acetate, tetrahydrofuran, dioxane, dichloromethane, dichloroethane or benzene) at a temperature ranging from room temperature to the boiling point of the reaction mixture, preferably at room temperature, to give compound (XXIII).

Compound (XXIII), which is identical with compound (XI) in Process 1, is converted into compound (XIV) as in Process 1 or 2 where compound (XI) is converted into compound (XIV).

Compound (XVII) used in Processes 4 and 5 can be prepared by either Process 6 or 7 shown below.

Reaction Scheme 6 (Process 6)

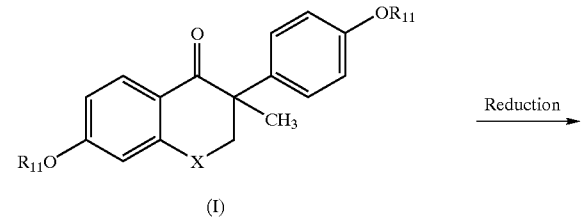

(I)

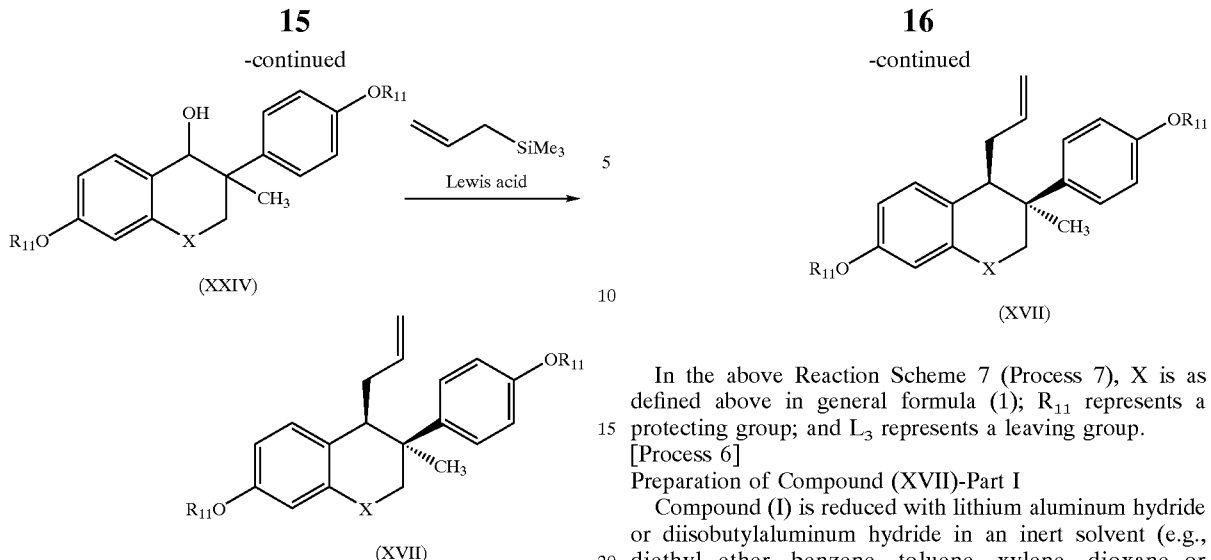

(XXIV)

(XVII)

In the above Reaction Scheme 6 (Process 6), X is as defined above in general formula (1); and $R_{11}$ represents a protecting group.

Reaction Scheme 7 (Process 7)

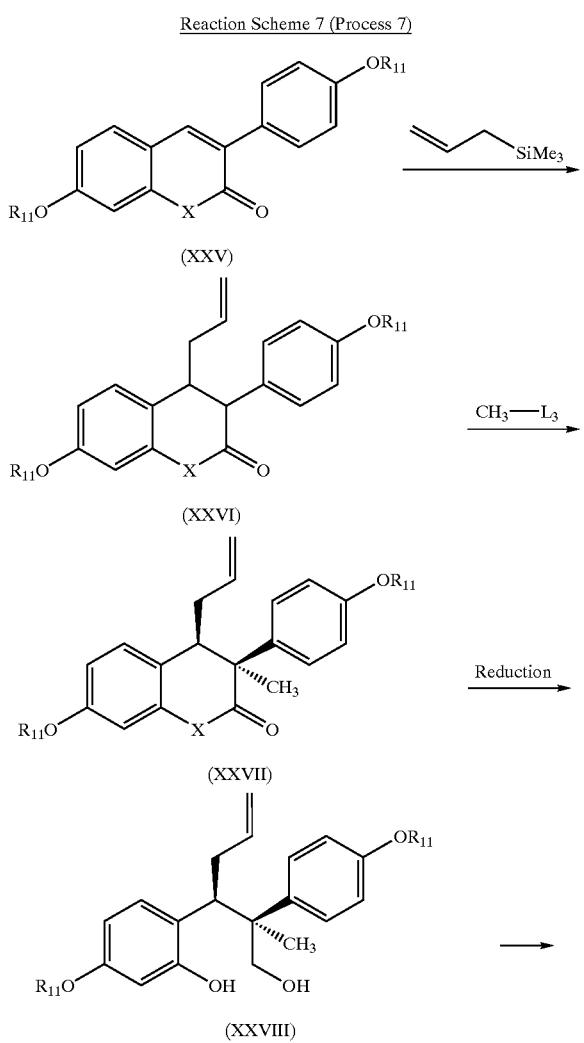

(XXV)

(XXVI)

(XXVII)

(XXVIII)

In the above Reaction Scheme 7 (Process 7), X is as defined above in general formula (1); $R_{11}$ represents a protecting group; and $L_3$ represents a leaving group.

[Process 6]

Preparation of Compound (XVII)-Part I

Compound (I) is reduced with lithium aluminum hydride or diisobutylaluminum hydride in an inert solvent (e.g., diethyl ether, benzene, toluene, xylene, dioxane or tetrahydrofuran) at a temperature ranging from −78° C. to the boiling point of the reaction mixture to give compound (XXIV).

In the presence of a Lewis acid such as zinc iodide, compound (XXIV) is reacted with allyltrimethylsilane in an inert solvent (e.g., tetrahydrofuran, dioxane, dichloromethane, dichloroethane or chloroform, preferably dichloroethane) at a temperature ranging from −78° C. to the boiling point of the reaction mixture, preferably from 0° C. to room temperature, to give compound (XVII).

[Process 7]

Preparation of Compound (XVII)-Part II

In the presence of anhydrous TBAF and, if necessary, accompanied by addition of HMPA, compound (XXV) is reacted with allyltrimethylsilane in an inert solvent (e.g., dimethylformamide, dimethyl sulfoxide, tetrahydrofuran, dioxane, dichloromethane, dichloroethane or chloroform) at a temperature ranging from −78° C. to the boiling point of the reaction mixture, preferably from 0° C. to room temperature, to give compound (XXVI).

In the presence of a base (e.g., lithium hexamethyldisilazide, n-butyllithium, s-butyllithium, sodium hydride), compound (XXVI) is reacted with an alkylating agent ($CH_3–L_3$) in an inert solvent (e.g., tetrahydrofuran, ether, dioxane, dichloromethane, chloroform, preferably tetrahydrofuran or dioxane) at a temperature ranging from −78° C. to the boiling point of the reaction mixture, preferably from −78° C. to room temperature, to give compound (XXVII).

Compound (XXVII) is reduced with lithium aluminum hydride in an inert solvent (e.g., tetrahydrofuran, dioxane or diethyl ether) at a temperature ranging from −78° C. to the boiling point of the reaction mixture to give compound (XXVIII).

Compound (XXVIII) is reacted with diethyl azodicarboxylate and triphenylphosphine in an inert solvent (e.g., toluene, dioxane, dimethylformamide, dimethyl sulfoxide, tetrahydrofuran, dichloromethane, dichloroethane or chloroform) at a temperature ranging from −78° C. to the boiling point of the reaction mixture, preferably from 0° C. to room temperature, to give compound (XVII).

Compound (XIV) given by the above Processes 1 to 5 may also be converted into a salt form because it has a carboxyl group. Pharmaceutically acceptable salts include, sodium, potassium and calcium salts. For example, a salt of compound (XIV) can be prepared as follows.

Sodium methoxide is added to compound (XIV) dissolved in an organic solvent (e.g., dry methanol) at an appropriate temperature, for example, at room temperature, and the resulting mixture is stirred for about 30 minutes to about 3 hours at the same temperature. After addition of an organic solvent such as dry diethyl ether, the reaction mixture is evaporated under reduced pressure to remove the solvent, thereby obtaining a salt of the compound.

The compound of the present invention exists as various enantiomers because it contains three asymmetric carbon atoms. To obtain a single stereoisomer, there are two techniques, one of which uses a chiral column to resolve a mixture of stereoisomers and the other involves asymmetric synthesis. The chiral column technique may be carried out using a column commercially available from DAICEL under the trade name of CHIRALPAK-OT(+), OP(+) or AD, or CHIRALCEL-OA, OB, OJ, OK, OC, OD, OF or OG, for example. Regarding asymmetric synthesis, the following will illustrate the asymmetric synthesis of the inventive compound with respect to an asymmetric carbon atom, to which a side chain carboxyl group is attached.

Reaction Scheme 8

(Process 8)

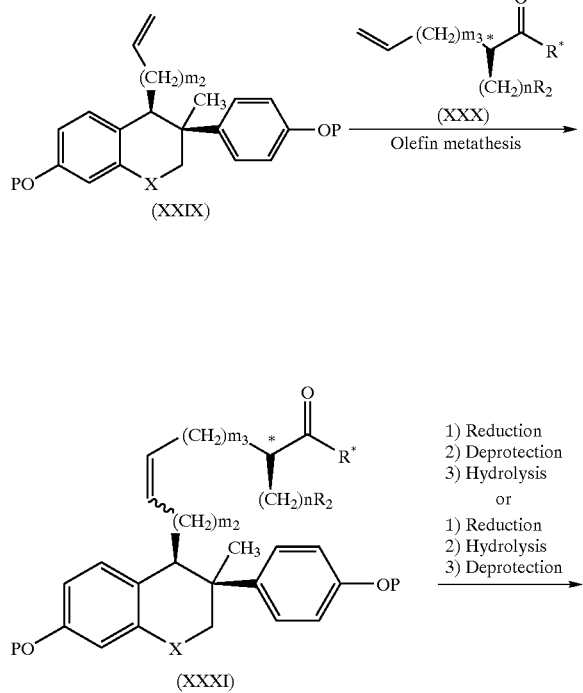

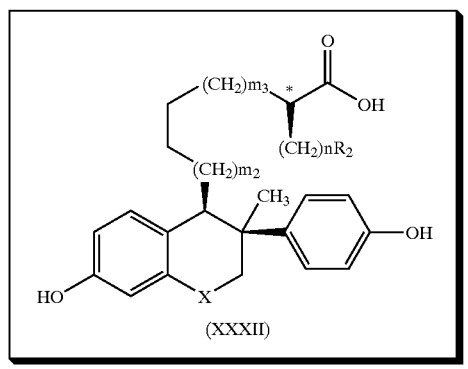

Reaction Scheme 9

(Process 9)

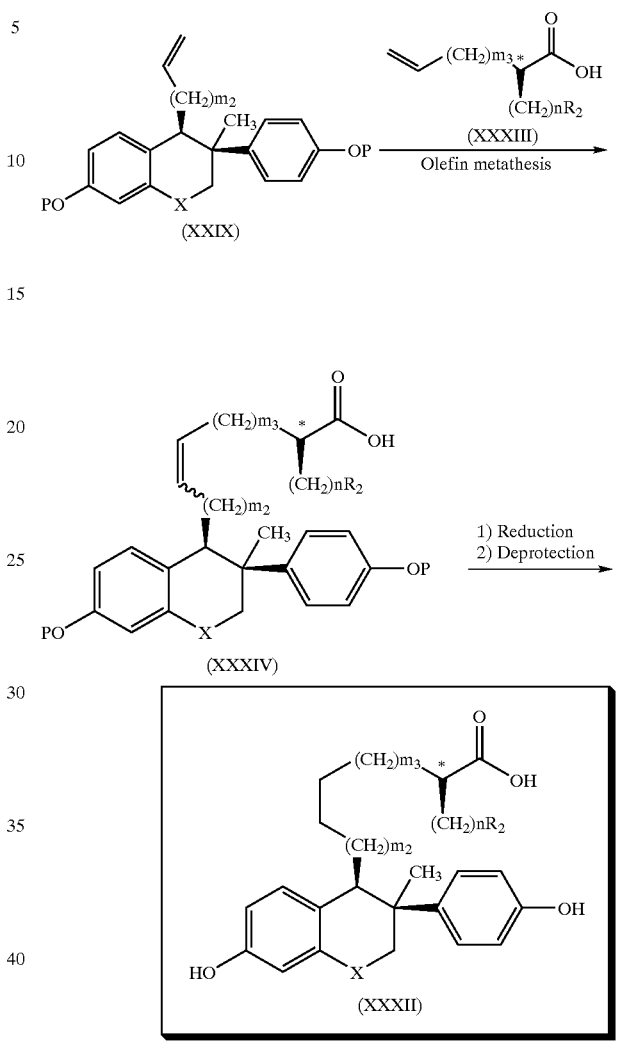

[Process 8]

In the presence of a catalyst such as benzylidene-bis (tricyclohexylphosphine)dichlororuthenium, compound (XXIX) is reacted with compound (XXX) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (XXXI).

Compound (XXXI) is then subjected to the following reactions in the order stated, (a) reduction, deprotection and hydrolysis or (b) reduction, hydrolysis and deprotection, to give compound (XXXII).

(a) Reduction, Deprotection and Hydrolysis

1) Reduction

In the presence of a catalyst (e.g., palladium on activated carbon, palladium hydroxide, platinum oxide or Wilkinson's catalyst), compound (XXXI) is hydrogenated in an inert solvent (e.g., methanol, ethanol, ethyl acetate, tetrahydrofuran, dioxane or benzene) at a temperature ranging from 0° C. to the boiling point of the reaction mixture, preferably at room temperature, to give a reduction product.

2) Deprotection

Next, deprotection of the phenolic hydroxyl group is carried out to give a deprotected product.

3) Hydrolysis

By way of example, if R* is a group of formula (XXXVIII), the deprotected product is further treated with lithium hydroxide, sodium hydroxide, lithium hydroxide plus hydrogen peroxide, sodium hydroxide plus hydrogen peroxide, or tetrabutylammonium hydroxide plus hydrogen peroxide in a solvent (e.g., a tetrahydrofuran/water mixture, a diethyl ether/water mixture, a dioxane/water mixture, a methanol/water mixture, an ethanol/water mixture) at a temperature ranging from room temperature to the boiling point of the reaction mixture, preferably at room temperature, to give compound (XXXII).

(b) Reduction, Hydrolysis and Deprotection

1) Reduction

In the presence of a catalyst (e.g., palladium on activated carbon, palladium hydroxide, platinum oxide or Wilkinson's catalyst), compound (XXXI) is hydrogenated in an inert solvent (e.g., methanol, ethanol, ethyl acetate, tetrahydrofuran, dioxane or benzene) at a temperature ranging from 0° C. to the boiling point of the reaction mixture, preferably at room temperature, to give a reduction product.

2) Hydrolysis

By way of example, if R* is a group of formula (XXXVIII), the reduction product is further treated with lithium hydroxide, sodium hydroxide, lithium hydroxide plus hydrogen peroxide, sodium hydroxide plus hydrogen peroxide, or tetrabutylammonium hydroxide plus hydrogen peroxide in a solvent (e.g., a tetrahydrofuran/water mixture, a diethyl ether/water mixture, a dioxane/water mixture, a methanol/water mixture, an ethanol/water mixture) at a temperature ranging from room temperature to the boiling point of the reaction mixture, preferably at room temperature, to give a carboxylic acid.

3) Deprotection

Next, deprotection of the phenolic hydroxyl group is carried out to give compound (XXXII).

[Process 9]

In the presence of a catalyst such as benzylidene-bis(tricyclohexylphosphine)dichlororuthenium, compound (XXIX) is reacted with compound (XXXIII) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (XXXIV).

In the presence of a catalyst (e.g., palladium on activated carbon, palladium hydroxide, platinum oxide or Wilkinson's catalyst), compound (XXXIV) is hydrogenated in an inert solvent (e.g., methanol, ethanol, ethyl acetate, tetrahydrofuran, dioxane or benzene) at a temperature ranging from 0° C. to the boiling point of the reaction mixture, preferably at room temperature, to give a reduction product.

Next, deprotection of the phenolic hydroxyl group is carried out to give compound (XXXII).

The chiral olefins of formulae (XXX) and (XXXIII) used in the above Processes 8 and 9, respectively, may be synthesized as follows (Reaction Scheme 10).

Reaction Scheme 10

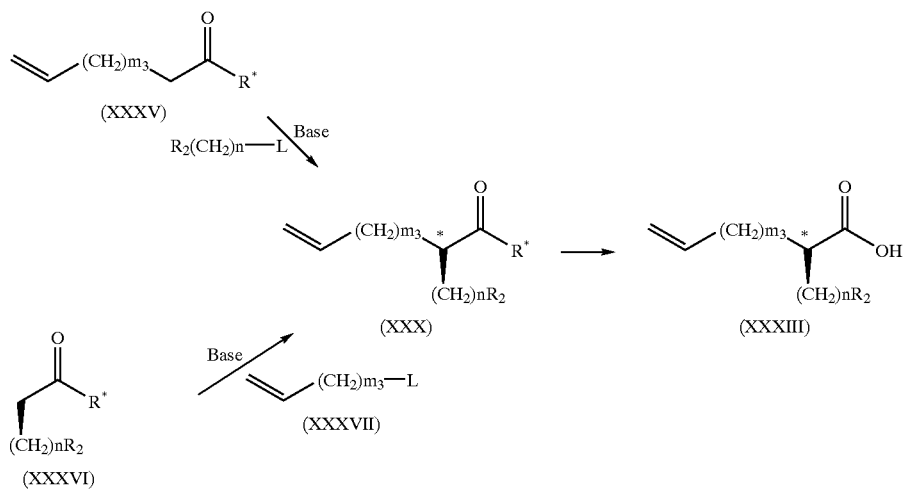

Examples of R* include:

(XXXVIII)

(XXXIV)

-continued

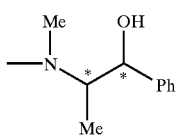
(XXXV)

In the above Reaction Schemes 8, 9 and 10 (Processes 8, 9 and 10), $R_2$, X, m and n are as defined above in general formula (1); R* represents a chiral auxiliary group; P represents a leaving group; L represents a leaving group; and $m_2$ and $m_3$ are integers that satisfy the relation $m=m_2+m_3+2$. The symbol R in formula (XXXIV) represents an alkyl group.

[Synthesis of Chiral Olefins]

In the presence of a base (e.g., lithium diisopropylamide, lithium hexamethyl-disilazide, sodium hexamethyl-disilazide, butyllithium) and HMPA, compound (XXXV) is reacted with $R_2(CH_2)_n$—L in an inert solvent (e.g., tetrahydrofuran, toluene, diethyl ether, hexane, preferably tetrahydrofuran) at a temperature ranging from –78° C. to the boiling point of the reaction mixture, preferably from –30° C. to room temperature, to give compound (XXX).

Alternatively, in the presence of a base (e.g., lithium diisopropylamide, lithium hexamethyl-disilazide, sodium hexamethyl-disilazide, butyllithium) and HMPA, compound (XXXVI) is reacted with compound (XXXVII) in an inert solvent (e.g., tetrahydrofuran, toluene, diethyl ether, hexane, preferably tetrahydrofuran) at a temperature ranging from –78° C. to the boiling point of the reaction mixture, preferably from –30° C. to room temperature, to give compound (XXX).

In the presence of a nucleophilic reagent (e.g., lithium hydroxide plus hydrogen peroxide, lithium hydroxide, sodium methoxide, sodium thioethoxide) or an acid (e.g., hydrochloric acid, sulfuric acid), compound (XXX) is hydrolyzed in an inert solvent (e.g., methanol, ethanol, tetrahydrofuran, water, preferably a tetrahydrofuran/water mixture) at a temperature ranging from –78° C. to the boiling point of the reaction mixture, preferably from room temperature to 50° C., to convert the chiral auxiliary group R* into OH.

In the case where each of $R_3$ and $R_4$ is an acyl group or an alkyl group, the synthesis can be carried out according to Process 9.

EXAMPLES

The present invention is more specifically explained by the following examples. However, it should be understood that the present invention is not limited to these examples in any manner. In order to explain the effectiveness of the compounds according to the present invention, typical compounds were tested for their anti-estrogenic activity in the test example shown below. Tables 1 to 3 show chemical structures of the compounds prepared in the Examples.

TABLE 1

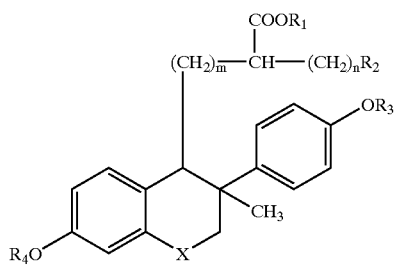

| Example No. | X | $R_1$ | $R_2$ | $R_3$ | $R_4$ | m | n |
|---|---|---|---|---|---|---|---|
| 8 | S | H | —$(CF_2)_3CF_3$ | H | H | 8 | 2 |
| 9 | S | H | —$(CF_2)_3CF_3$ | H | H | 8 | 3 |
| 10 | S | H | —$(CF_2)_3CF_3$ | H | H | 8 | 4 |
| 11 | S | H | —$(CF_2)_3CF_3$ | H | H | 9 | 2 |
| 12 | S | H | —$(CF_2)_3CF_3$ | H | H | 9 | 3 |
| 13 | O | H | —$(CF_2)_3CF_3$ | H | H | 8 | 2 |
| 14 | O | H | —$(CF_2)_3CF_3$ | H | H | 9 | 2 |

TABLE 2

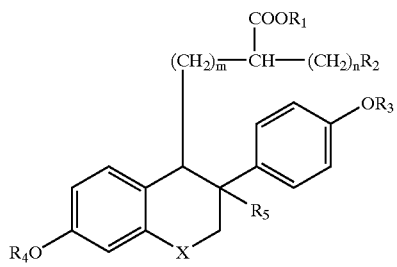

| Example No. | X | $R_1$ | $R_2$ | $R_3$ | $R_4$ | $R_5$ | m | n |
|---|---|---|---|---|---|---|---|---|
| 15 | O | H | —$(CF_2)_3CF_3$ | H | H | Me | 8 | 3 |
| 16 | O | H | —$(CF_2)_3CF_3$ | H | H | Me | 9 | 3 |
| 27 | S | Na | —$(CF_2)_3CF_3$ | H | H | Me | 8 | 2 |
| 28 | O | Na | —$(CF_2)_3CF_3$ | H | H | Me | 9 | 2 |

TABLE 3

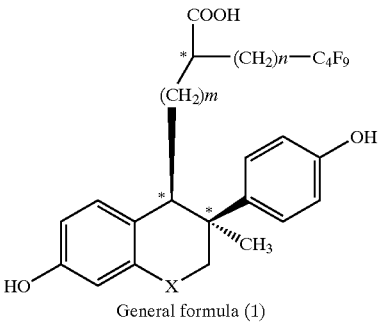

General formula (1)

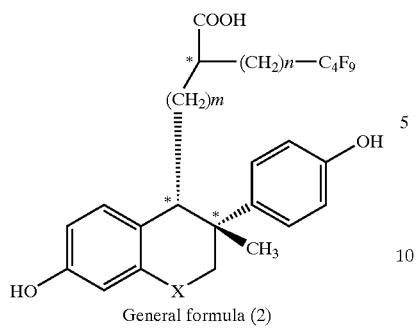

General formula (2)

| Example No. | Formula | X | m | n |
|---|---|---|---|---|
| 19, Peak1 | (1) | S | 8 | 2 |
| 19, Peak2 | (1) | S | 8 | 2 |
| 21, Peak1 | (2) | S | 8 | 2 |
| 21, Peak2 | (2) | S | 8 | 2 |
| 24, Peak1 | (1) or (2) | O | 9 | 2 |
| 24, Peak2 | (1) or (2) | O | 9 | 2 |
| 26, Peak1 | (1) or (2) | O | 9 | 2 |
| 26, Peak2 | (1) or (2) | O | 9 | 2 |

Example 1

Synthesis of 1-iodo-4,4,5,5,6,6,7,7,7-nonafluoroheptane (Step 1)

1-Iodo-3,3,4,4,5,5,6,6,6-nonafluorohexane (10.0 g, 26.2 mmol) and sodium cyanide (3.85 g, 78.6 mmol) were stirred in dimethyl sulfoxide (50 ml) for 30 minutes at 60° C. Water was added to the reaction mixture, which was then extracted with ether. The resulting organic layer was washed with water and saturated aqueous sodium chloride, and then dried over anhydrous magnesium sulfate. The solvent was distilled off to give 4,4,5,5,6,6,7,7,7-nonafluoroheptanecarbonitrile (4.7 g, Yield 66%) as a brown oil.

$^1$H-NMR (300 MHz, CDCl$_3$): δ 2.72 (t, 2H), 2.63–2.42 (m, 2H).

(Step 2)

4,4,5,5,6,6,7,7,7-Nonafluoroheptanecarbonitrile (4.7 g, 17.2 mmol) was stirred in concentrated sulfuric acid (15 ml) for 3 hours at room temperature, cooled to 0° C. and mixed with water (15 ml), followed by heating under reflux for 12 hours. The reaction mixture was extracted with dichloromethane and the resulting organic layer was washed with water and saturated aqueous sodium chloride and then dried over anhydrous magnesium sulfate. The solvent was distilled off to give 4,4,5,5,6,6,7,7,7-nonafluoroheptanoic acid (5.1 g, quantitative) as an oil.

$^1$H-NMR(300 MHz, CDCl$_3$): δ 2.71 (t, 2H), 2.62–2.38 (m, 2H).

(Step 3)

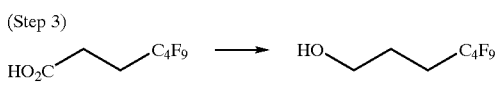

Borane-methyl sulfide complex (5.2 ml, 52.2 mmol) was slowly added to a solution of 4,4,5,5,6,6,7,7,7-nonafluoroheptanoic acid (5.10 g, 17.4 mmol) in anhydrous tetrahydrofuran (50 ml) at −50° C. The reaction mixture was stirred for 4 hours at room temperature and cooled to 0° C., followed by addition of methanol. After distilling off the solvent, the residue was purified by silica gel column chromatography (eluent: ethyl acetate/hexane=1/5→1/3) to give 4,4,5,5,6,6,7,7,7-nonafluoroheptan-1-ol (4.7 g, Yield 97%) as a colorless oil.

$^1$H-NMR(300 MHz, CDCl$_3$): δ 3.75 (t, 2H), 2.32–2.13 (m, 2H), 1.93–1.80 (m, 2H), 1.38 (bs, 1H).

(Step 4)

Methanesulfonyl chloride (2.8 ml, 36.72 mmol) was added to a solution of 4,4,5,5,6,6,7,7,7-nonafluoroheptan-1-ol (6.0 g, 21.6 mmol) and triethylamine (6.0 ml, 43.2 mmol) in dichloromethane (60 ml) at 0° C., followed by stirring for 1 hour. After the reaction was completed, water was added to the reaction mixture, which was then extracted with dichloromethane. The organic layer was washed with water and saturated aqueous sodium chloride, and then dried over anhydrous magnesium sulfate. After distilling off the solvent, the residue was purified by silica gel column chromatography (eluent: ethyl acetate/hexane=1/3) to give 1-methanesulfonyloxy-4,4,5,5,6,6,7,7,7-nonafluoroheptane (6.73 g, Yield 92.2%) as a colorless oil.

$^1$H-NMR(300 MHz, CDCl$_3$): δ 4.34 (t, 2H), 3.05 (s, 3H), 2.35–2.20 (m, 2H), 2.19–2.09 (m, 2H).

(Step 5)

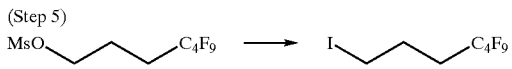

1-Methanesulfonyloxy-4,4,5,5,6,6,7,7,7-nonafluoroheptane (6.7 g, 18.8 mmol) and sodium iodide (8.5 g, 56.4 mmol) were stirred in acetone (400 ml) for 12 hours under heating. After the reaction was completed, water was added to the reaction mixture, which was then extracted with ether. The organic layer was washed with water and saturated aqueous sodium chloride, and then dried over anhydrous magnesium sulfate. The solvent was distilled off to give 1-iodo-4,4,5,5,6,6,7,7,7-nonafluoroheptane (6.33 g, Yield 87%) as a colorless oil.

$^1$H-NMR(300 MHz, CDCl$_3$): δ 3.22 (t, 2H), 2.31–2.08 (m, 4H).

Example 2

Synthesis of 1-iodo-5,5,6,6,7,7,8,8,8-nonafluorooctane (Step 1)

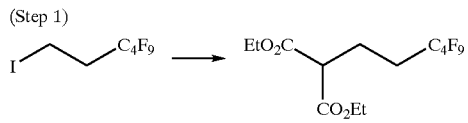

Anhydrous tetrahydrofuran (200 ml) was added to 60% sodium hydride (2.78 g, 69.52 mmol) and the resulting mixture was cooled to 0° C. Diethyl malonate (12.18 ml, 80.22 mmol) was slowly added dropwise to this mixture, which was then stirred for 1 hour at room temperature. A solution of 1-iodo-3,3,4,4,5,5,6,6,6-nonafluorohexane (20.0 g, 53.48 mmol) in anhydrous tetrahydrofuran (50 ml) was then slowly added dropwise to the mixture, followed by stirring for 12 hours at room temperature. Water was added to the reaction mixture, which was then extracted twice with ethyl acetate. The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/50) to give diethyl 2-(3,3,4,4,5,5,6,6,6-nonafluorohexyl)malonate (19.4 g, Yield 89%).

$^1$H-NMR(300 MHz, CDCl$_3$): δ 4.24(q, 4H), 3.41(t, 1H), 2.30–2.19(m, 4H), 1.28(t, 6H).

(Step 2)

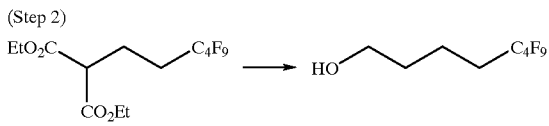

A solution of potassium hydroxide (53.59 g, 955.09 mmol) in water (200 ml) was added to a solution of diethyl 2-(3,3,4,4,5,5,6,6,6-nonafluorohexyl)malonate (19.4 g, 47.75 mmol) in ethanol (400 ml), followed by stirring for 6 hours at 60° C. After the reaction was completed, the reaction mixture was adjusted to pH 5 at room temperature by slowly adding 1N hydrochloric acid dropwise, and then extracted twice with ethyl acetate. The combined organic layers were washed with saturated aqueous sodium chloride and dried over anhydrous magnesium sulfate. After distilling off the solvent, the residue was stirred in dimethyl sulfoxide for 18 hours at 170° C. After the reaction was completed, water was added to the reaction mixture, which was then extracted three times with ethyl acetate. The combined organic layers were washed with water and saturated aqueous sodium chloride, and then dried over anhydrous magnesium sulfate. After distilling off the solvent, anhydrous tetrahydrofuran (200 ml) was added to the residue and the resulting mixture was cooled to −30° C. Borane-methyl sulfide complex (10M in THF, 8.5 ml, 85 mmol) was slowly added dropwise to this mixture, followed by stirring for 3 hours at room temperature. After treatment with methanol at 0° C., water was added to the reaction mixture, which was then extracted twice with ethyl acetate. The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/20) to give 5,5,6,6,7,7,8,8,8-nonafluorooctan-1-ol (9.4 g, Yield 60%).

$^1$H-NMR(300 MHz, CDCl$_3$): δ 3.69(t, 2H), 2.20–2.02(m, 2H), 1.77–1.58(m, 4H), 1.52(bs, 1H).

(Step 3)

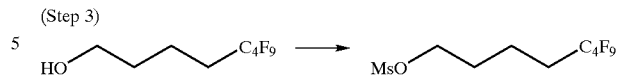

A solution of 5,5,6,6,7,7,8,8,8-nonafluorooctan-1-ol (7.8 g, 26.70 mmol) in dichloromethane (150 ml) was cooled to 0° C. Triethylamine (9.29 ml, 66.75 mmol) and methanesulfonyl chloride (2.48 ml, 32.04 mmol) were added dropwise to the solution, followed by stirring for 1 hour. After the reaction was completed, water was added to the reaction mixture, which was then extracted twice with dichloromethane. The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/4) to give 1-methanesulfonyloxy-5,5,6,6,7,7,8,8,8-nonafluorooctane (8.5 g, Yield 86%).

$^1$H-NMR(300 MHz, CDCl$_3$): δ 4.26(t, 2H), 3.02(s, 3H), 2.22–2.04(m, 2H), 1.91–1.71(m, 4H).

(Step 4)

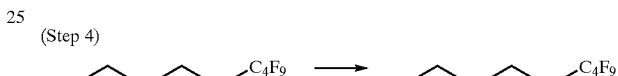

Sodium iodide (10.32 g, 68.88 mmol) was added to a solution of 1-methanesulfonyloxy-5,5,6,6,7,7,8,8,8-nonafluorooctane (8.5 g, 22.96 mmol) in acetone (300 ml), followed by heating under reflux for 12 hours. After the reaction was completed, water was added to the reaction mixture, which was then extracted twice with ethyl acetate. The combined organic layers were washed with 1% aqueous sodium thiosulfate and saturated aqueous sodium chloride, and then dried over anhydrous magnesium sulfate. The solvent was distilled off to give 1-iodo-5,5,6,6,7,7,8,8,8-nonafluorooctane (8.6 g, Yield 93%).

$^1$H-NMR(300 MHz, CDCl$_3$): δ 3.20(t, 2H), 2.17–2.01(m, 2H), 1.97–1.87(m, 2H), 1.82–1.70(m, 2H).

Example 3

Synthesis of ethyl 2-(3,3,4,4,5,5,6,6,6-nonafluorohexyl)-8-nonenoate (Step 1)

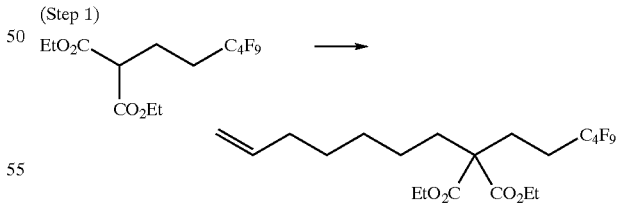

The diethyl 2-(3,3,4,4,5,5,6,6,6-nonafluorohexyl)-malonate prepared in Step 1 of Example 2 (1.2 g, 3.0 mmol) was slowly added dropwise to a suspension of 60% sodium hydride (288 mg, 12 mmol) in anhydrous dimethyl sulfoxide (20 ml) at 0° C., followed by stirring for 1 hour at room temperature. After 7-iodohept-1-ene (795 mg, 2.5 mmol) was slowly added dropwise, the reaction mixture was stirred for 12 hours at room temperature. Water was added to the reaction mixture, which was then extracted twice with ethyl acetate. The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/40) to give diethyl 2-(6-heptenyl)-2-(3,3,4,4,5,5,6,6,6-nonafluorohexyl)malonate (1.08 g, Yield 73%).

$^1$H-NMR(300 MHz, CDCl$_3$): δ 5.76 (m, 1H), 5.02–4.85 (m, 2H), 4.20 (q, 4H), 2.20–1.11 (m, 20H).

(Step 2)

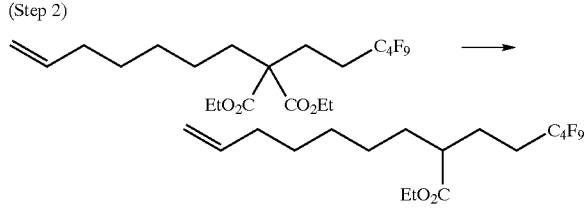

A solution of diethyl 2-(6-heptenyl)-2-(3,3,4,4,5,5,6,6,6-nonafluorohexyl)malonate (1.05 g, 2.1 mmol) in dimethyl sulfoxide (10 ml) was stirred with lithium chloride (0.18 g, 4.2 mmol) and water (0.038 ml, 2.1 mmol) for 5 hours at a temperature of 170° C. to 180° C. Water was added to the reaction mixture, which was then extracted twice with ethyl acetate. The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/40) to give ethyl 2-(3,3,4,4,5,5,6,6,6-nonafluorohexyl)-8-nonenoate (0.80 g, Yield 89%).

$^1$H-NMR(300 MHz, CDCl$_3$): δ 5.75(m, 1H), 5.02–4.86 (m, 2H), 4.15(q, 2H, J=7.2 Hz), 2.40(m, 1H), 2.19–1.12(m, 17H).

Example 4

Synthesis of ethyl 2-(4,4,5,5,6,6,7,7,7-nonafluoroheptyl)-8-nonenoate (Step 1)

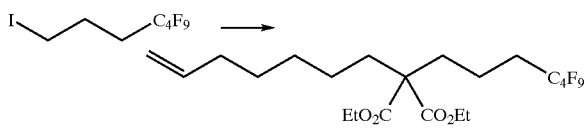

60% sodium hydride (0.54 g, 13.5 mmol) was added to a solution of diethyl 2-(6-heptenyl)malonate (3.0 g, 11.7 mmol) in tetrahydrofuran (30 ml) followed by stirring for 30 minutes at room temperature. 1-Iodo-4,4,5,5,6,6,7,7,7-nonafluoroheptane (5.45 g, 14.04 mmol) was added to the mixture followed by stirring for 12 hours at room temperature. After the reaction was completed, water was added to the reaction mixture, which was then extracted with ethyl acetate. The organic layer was washed with water and saturated aqueous sodium chloride, and then dried over anhydrous magnesium sulfate. After distilling off the solvent, the residue was purified by silica gel column chromatography (eluent: ethyl acetate/hexane=1/25) to give diethyl 2-(6-heptenyl)-2-(4,4,5,5,6,6,7,7,7-nonafluoroheptyl)malonate (6.14 g, quantitative) as a colorless oil.

$^1$H-NMR(300 MHz, CDCl$_3$): δ 5.76 (m, 1H), 5.00–4.88 (m, 2H), 4.18 (q, 4H), 2.15–1.81 (m, 8H), 1.41–1.08 (m, 14H).

(Step 2)

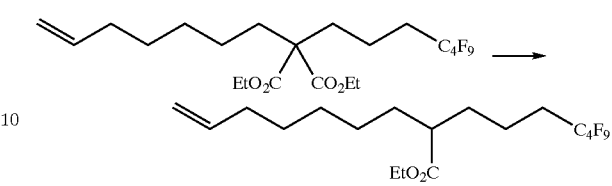

Lithium chloride (985 mg, 23.24 mmol) and water (0.21 ml, 11.62 mmol) were added to a solution of diethyl 2-(6-heptenyl)-2-(4,4,5,5,6,6,7,7,7-nonafluoroheptyl)malonate (6.0 g, 11.62 mmol) in dimethyl sulfoxide (40 ml) followed by stirring for 12 hours at a temperature of 160° C. to 180° C. After the reaction was completed, water was added to the reaction mixture, which was then extracted with ethyl acetate. The organic layer was washed with water and saturated aqueous sodium chloride, and then dried over anhydrous magnesium sulfate. After distilling off the solvent, the residue was purified by silica gel column chromatography (eluent: ethyl acetate/hexane=1/40→1/30) to give ethyl 2-(4,4,5,5,6,6,7,7,7-nonafluoroheptyl)-8-nonenoate (2.3 g, Yield 44%) as a colorless oil.

$^1$H-NMR(300 MHz, CDCl$_3$): δ 5.80 (m, 1H), 5.02–4.90 (m, 2H), 4.11 (q, 2H), 2.30 (m, 1H), 2.15–1.92 (m, 4H), 1.72–1.08 (m, 15H).

Example 5

Synthesis of ethyl 2-(5,5,6,6,7,7,8,8,8-nonafluorooctyl)-8-nonenoate (Step 1)

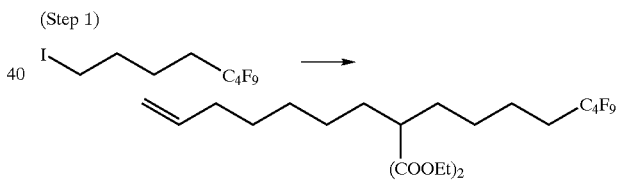

A solution of diethyl 2-(6-heptenyl)malonate (3.83 g, 14.92 mmol) in anhydrous tetrahydrofuran (50 ml) was slowly added dropwise to a suspension of 60% sodium hydride (0.52 g, 12.94 mmol) in anhydrous tetrahydrofuran (150 ml) at 0° C., and the resulting mixture was stirred for 1 hour. The 1-iodo-5,5,6,6,7,7,8,8,8-nonafluorooctane prepared in Example 2 (4.0 g, 9.95 mmol) was dissolved in anhydrous tetrahydrofuran (50 ml) and then slowly added dropwise to the mixture, followed by stirring for 2 days at room temperature. After the reaction was completed, water was added to the reaction mixture, which was then extracted twice with ethyl acetate. The combined organic layers were washed with water and saturated aqueous sodium chloride, and then dried over anhydrous magnesium sulfate. After distilling off the solvent, the residue was purified by silica gel column chromatography (eluent: ethyl acetate/hexane= 1/30) to give diethyl 2-(6-heptenyl)-2-(5,5,6,6,7,7,8,8,8-nonafluorooctyl)malonate (4.7 g, Yield 89%).

$^1$H-NMR(300 MHz, CDCl$_3$): δ 5.78(m, 1H), 5.01–4.92 (m, 2H), 4.19(q, 4H), 2.13–1.97(m, 4H), 1.92–1.84(m, 4H), 1.67–1.57(m, 2H), 1.41–1.13(m, 14H).

(Step 2)

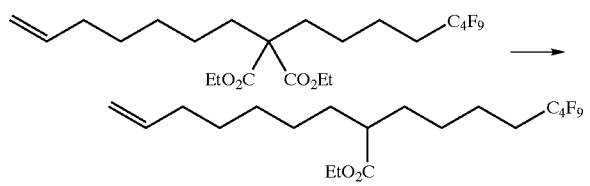

Lithium chloride (0.75 g, 17.72 mmol) and water (0.16 ml, 8.86 mmol) were added to a solution of diethyl 2-(6-heptenyl)-2-(5,5,6,6,7,7,8,8,8-nonafluorooctyl)malonate (4.7 g, 8.86 mmol) in dimethyl sulfoxide (100 ml) followed by stirring for 12 hours at a temperature of 170° C. to 180° C. After the reaction was completed, water was added to the reaction mixture, which was then extracted twice with ethyl acetate (100 ml). The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/50) to give ethyl 2-(5,5,6,6,7,7,8,8,8-nonafluorooctyl)-8-nonenoate (2.01 g, Yield 49.5%).

$^1$H-NMR(300 MHz, CDCl$_3$): δ 5.78(m, 1H), 5.02–4.91 (m, 2H), 4.13(q, 2H), 2.32(m, 1H), 2.11–1.95(m, 4H), 1.68–1.22(m, 17H).

Example 6

Synthesis of ethyl 2-(3,3,4,4,5,5,6,6,6-nonafluorohexyl)-9-decenoate

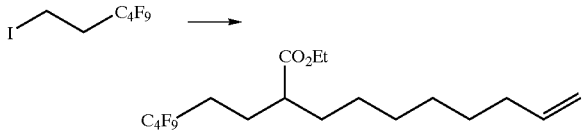

Starting with 1-iodo-3,3,4,4,5,5,6,6,6-nonafluorohexane, diethyl malonate and 8-iodooct-1-ene, the analogous procedure as shown in Example 3, 4 or 5 was repeated to give ethyl 2-(3,3,4,4,5,5,6,6,6-nonafluorohexyl)-9-decenoate.

$^1$H-NMR(300 MHz, CDCl$_3$): δ 5.80 (m, 1H), 4.96 (m, 2H), 4.15 (q, 2H, J=8.1 Hz), 2.40 (m, 1H), 2.15–1.65 (m, 6H), 1.60–1.26 (m, 13H).

Example 7

Synthesis of ethyl 2-(4,4,5,5,6,6,7,7,7-nonafluoroheptyl)-9-decenoate

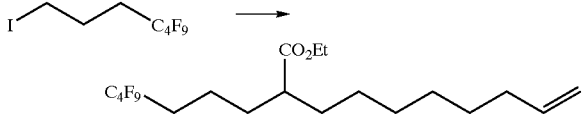

Starting with the 1-iodo-4,4,5,5,6,6,7,7,7-nonafluoroheptane prepared in Example 1, diethyl malonate and 8-bromooct-1-ene, a procedure analogous to that as shown in Example 3, 4 or 5 was repeated to give ethyl 2-(4,4,5,5,6,6,7,7,7-nonafluoroheptyl)-9-decenoate.

$^1$H-NMR(300 MHz, CDCl$_3$): δ 5.80(m, 1H), 5.02–4.90 (m, 2H), 4.14(q, 2H, J=7.2 Hz), 2.34(m, 1H), 2.19–1.98(m, 4H), 1.74–1.54(m, 4H), 1.42–1.24(m, 13H).

Example 8

Synthesis of 10-[(3RS,4RS)-7-hydroxy-3-(4-hydroxyphenyl)-3-methylthiochroman-4-yl]-2-(3,3,4,4,5,5,6,6,6-nonafluorohexyl)decanoic acid (Step 1)

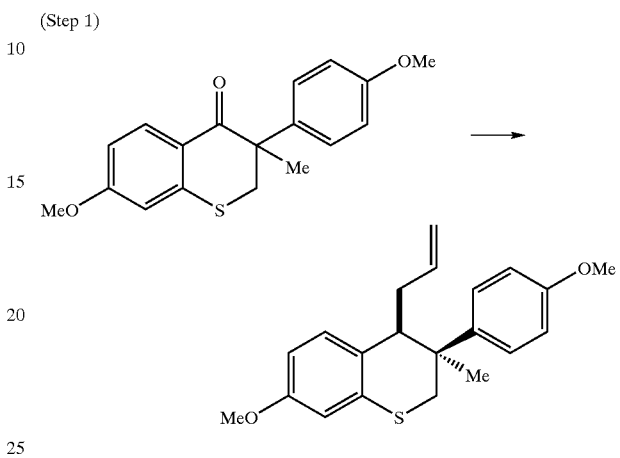

A solution of ketone (30.0 g, 95.5 mmol) in anhydrous tetrahydrofuran (200 ml) was added dropwise to a solution of lithium aluminum hydride (2.17 g, 57.1 mmol) in anhydrous tetrahydrofuran (200 ml) at −78° C. over 2 hours under argon atmosphere, followed by stirring for 2 hours. Ethyl acetate, methanol and 2N aqueous hydrochloric acid were added sequentially to the reaction mixture, which was then filtered through cellite. After extraction with ethyl acetate, the organic layer was washed with saturated aqueous sodium bicarbonate, water and saturated aqueous sodium chloride, and then dried over anhydrous magnesium sulfate. After distilling off the solvent, the resulting residue (30.05 g) was dissolved in 1,2-dichloroethane (600 ml) and then mixed with allyltrimethylsilane (30.1 ml, 190 mmol). Zinc iodide (36.4 g, 114 mmol) was added to this solution at 0° C. under argon atmosphere, and the resulting mixture was stirred for 5 hours at 40° C. and further stirred for 12 hours at room temperature. Water and dilute hydrochloric acid were added sequentially to this mixture, which was then extracted with ethyl acetate. The organic layer was washed with saturated aqueous sodium bicarbonate, water and saturated aqueous sodium chloride, and then dried over anhydrous magnesium sulfate. After distilling off the solvent, the residue was purified by silica gel flash column chromatography (hexane/ethyl acetate=100/1) to give (3RS,4RS)-7-methoxy-3-(4-methoxyphenyl)-3-methyl-4-(2-propenyl) thiochroman (22.2 g, Yield 68% for 2 steps).

$^1$H-NMR (270 MHz, CDCl$_3$): δ 7.31 (d, J=9 Hz, 2H, Ar—H), 6.91 (d, J=9 Hz, 2H, Ar—H), 6.90 (d, J=9 Hz, 1H, Ar—H), 6.72 (d, J=2 Hz, 1H, Ar—H), 6.56 (dd, J=9, 2 Hz, 1H, Ar—H), 5.54–5.48 (m, 1H, olefin-H), 4.82 (d, J=11 Hz, 1H, olefin-H), 4.66 (d, J=17 Hz, 1H, olefin-H), 3.83 (s, 3H, OCH$_3$), 3.78 (s, 3H, OCH$_3$), 3.65 (d, J=12 Hz, 1H, C2-H), 3.00 (d, J=12 Hz, 1H, C2-H), 2.87 (m, 1H, C4-H), 1.90 (m, 2H, allylic-CH$_2$), 1.23 (s, 3H, C3-CH$_3$).

(Step 2)

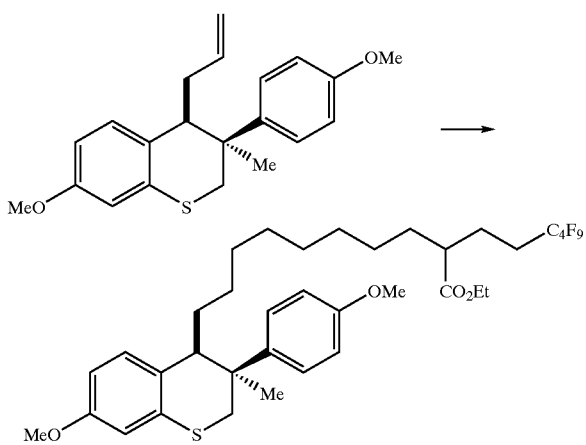

Benzylidenebis(tricyclohexylphosphine)-dichlororuthenium (191 mg, 0.232 mmol) was added to a dichloromethane (30 ml) solution of (3RS,4RS)-7-methoxy-3-(4-methoxyphenyl)-3-methyl-4-(2-propenyl)thiochroman (350 mg, 1 mmol) and the ethyl 2-(3,3,4,4,5,5,6,6,6-nonafluorohexyl)-8-nonenoate prepared in Example 3 (0.8 g, 1.9 mmol), followed by heating under reflux for 12 hours. The reaction mixture was concentrated under reduced pressure and the resulting residue was purified by silica gel column chromatography (eluent: ethyl acetate/hexane=1/30→1/20) to give the desired olefin (0.55 g, Yield 72%) as an oil.

10% Palladium carbon (70 mg) was added to a solution of the thus prepared olefin (0.5 g, 0.67 mmol) in ethyl acetate (50 ml) followed by stirring for 4 hours at room temperature under hydrogen atmosphere. The reaction mixture was filtered and the resulting filtrate was concentrated under reduced pressure to give ethyl 10-[(3RS,4RS)-7-methoxy-3-(4-methoxyphenyl)-3-methylthiochroman-4-yl]-2-(3,3,4,4,5,5,6,6,6-nonafluorohexyl)decanoate (0.5 g, quantitative) as a colorless oil.

$^1$H-NMR(300 MHz, CDCl$_3$): δ 7.31(d, 2H, J=8.7 Hz), 6.96–6.85(m,3H), 6.75(d, 1H), 6.58(dd,1H), 4.16(q,2H), 3.84(s,3H), 3.80(s,3H), 3.65(d,1H), 2.99(d,1H), 2.75(bs, 1H), 2.38(m,1H), 2.20–0.94(m,26H).

(Step 3)

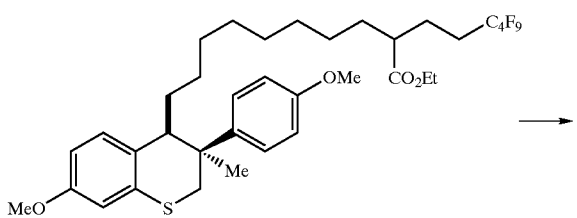

A solution of ethyl 10-[(3RS,4RS)-7-methoxy-3-(4-methoxyphenyl)-3-methylthiochroman-4-yl]-2-(3,3,4,4,5,5,6,6,6-nonafluorohexyl)decanoate (0.5 g, 0.67 mmol) in dichloromethane (10 mL) was cooled to −78° C. To this solution, a solution of boron tribromide in dichloromethane (1M, 5.37 ml) was slowly added dropwise, and the resulting mixture was stirred for 1 hour. The reaction vessel was then transferred to an ice-bath and the reaction mixture was further stirred for 3 hours. After the reaction was completed, water was added to the reaction mixture, which was then extracted with dichloromethane and dried over anhydrous magnesium sulfate. After distilling off the solvent, the residue was purified by silica gel column chromatography (eluent: hexane/ethyl acetate=20/1) to give ethyl 10-[(3RS,4RS)-7-hydroxy-3-(4-hydroxyphenyl)-3-methylthiochroman-4-yl]-2-(3,3,4,4,5,5,6,6,6-nonafluorohexyl)decanoate (0.4 g, Yield 84%) as a foam.

$^1$H-NMR(300 MHz, CDCl$_3$): δ 7.25(d, 2H, J=8.7 Hz), 6.92–6.80(m,3H), 6.69(d, 1H), 6.51(dd,1H), 5.60(s,0.5H), 5.50(s,0.5H), 4.88(s,0.5H), 4.85(s, 0.5H), 4.20(q,2H), 3.61 (d,1H), 2.98(d,1H), 2.68(bs,1H), 2.40(m,1H), 2.15–0.95(m, 26H).

(Step 4)

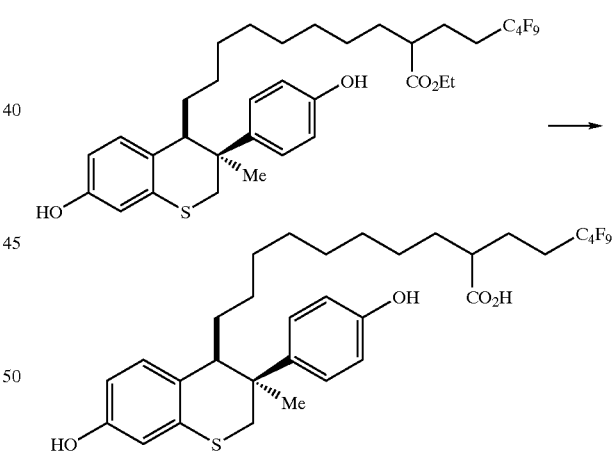

Ethyl 10-[(3RS,4RS)-7-hydroxy-3-(4-hydroxyphenyl)-3-methylthiochroman-4-yl]-2-(3,3,4,4,5,5,6,6,6-nonafluorohexyl)decanoate (0.38 g, 0.53 mmol) and sodium hydroxide (170 mg, 4.2 mmol) were added to an ethanol/water mixture (2:1, 15 ml), followed by heating under reflux for 4 hours. After the reaction mixture was neutralized with 1N hydrochloric acid, the solvent was distilled off and the resulting residue was diluted with water, adjusted to pH 2–3 with 1N hydrochloric acid, and then extracted twice with ethyl acetate. The combined organic layers were washed with saturated aqueous sodium chloride and dried over anhydrous magnesium sulfate. After distilling off the solvent, the residue was purified by silica gel column chromatography (eluent: ethyl acetate/hexane=1/4) to give 10-[(3RS,4RS)-7-hydroxy-3-(4-hydroxyphenyl)-3-methylthiochroman-4-yl]-2-(3,3,4,4,5,5,6,6,6-nonafluorohexyl)decanoic acid (260 mg, Yield 87%) as a colorless foam.

$^1$H-NMR(300 MHz, MeOH-d$_4$): δ 7.26 (d, 2H, J=8.8 Hz), 6.88 (d, 1H, J=8.3 Hz), 6.80 (d, 2H, J=8.7 Hz) 6.59 (d, 1H, J=2.4 Hz), 6.50 (dd, 1H, J=8.2 Hz, J$_2$=2.4 Hz), 3.64 (d, 1H, J=11.7 Hz), 2.98 (d, 1H, J=11.7 Hz), 2.68 (bs, 1H), 2.41 (m, 1H), 2.25–0.95 (m, 23H)

Mass (ESI): 689(M+1).

Example 9

Synthesis of 10-[(3RS,4RS)-7-hydroxy-3-(4-hydroxyphenyl)-3-methylthiochroman-4-yl]-2-(4,4,5,5,6,6,7,7,7-nonafluoroheptyl)decanoic acid

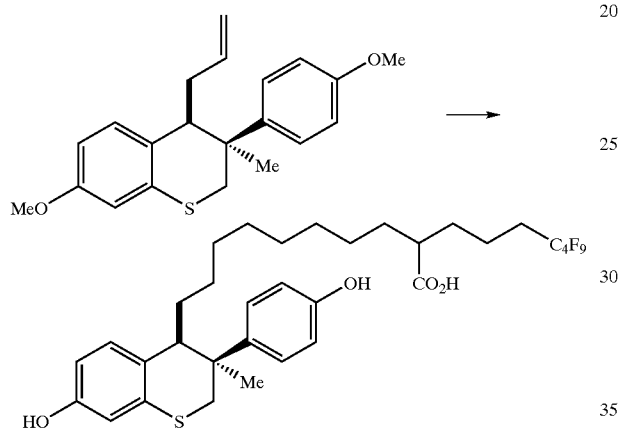

Starting with the allyl compound prepared in Example 8 and the ethyl 2-(4,4,5,5,6,6,7,7,7-nonafluoroheptyl)-8-nonenoate prepared in Example 4, a procedure analogous to that as shown in Example 8 was repeated to give 10-[(3RS,4RS)-7-hydroxy-3-(4-hydroxyphenyl)-3-methylthiochroman-4-yl]-2-(4,4,5,5,6,6,7,7,7-nonafluoroheptyl)decanoic acid.

$^1$H-NMR(300 MHz, CDCl$_3$): δ 7.19(d, 2H), 6.92~6.78(m, 3H), 6.65(d, 1H), 6.55(dd, 1H), 3.62(d, 1H), 2.95(d, 1H), 2.65(bs, 1H), 2.35(m, 1H), 2.17–1.95(m, 2H), 1.70~1.40(m, 6H), 1.32~0.90(m, 17H).

Mass(ESI): 725(M+Na)

Example 10

Synthesis of 10-[(3RS,4RS)-7-hydroxy-3-(4-hydroxyphenyl)-3-methylthiochroman-4-yl]-2-(5,5,6,6,7,7,8,8,8-nonafluorooctyl)decanoic acid

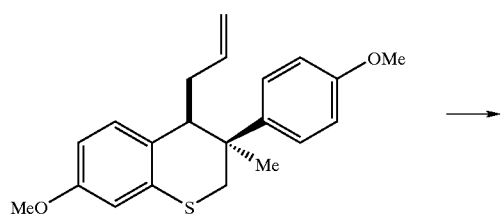

Starting with the allyl compound prepared in Example 8 and the ethyl 2-(5,5,6,6,7,7,8,8,8-nonafluorooctyl)-8-nonenoate prepared in Example 5, a procedure analogous to that as shown in Example 8 was repeated to give 10-[(3RS,4RS)-7-hydroxy-3-(4-hydroxyphenyl)-3-methylthiochroman-4-yl]-2-(5,5,6,6,7,7,8,8,8-nonafluorooctyl)decanoic acid.

$^1$H-NMR(300 MHz, CDCl$_3$): δ 7.23(d, 2H, J=8.6 Hz), 6.87–6.81(m, 3H), 6.66(d, 1H, J=2.2 Hz), 6.49(dd, 1H, J$_1$=8.0 Hz, J$_2$=2.3 Hz), 3.62(d, 1H, J=11.6 Hz), 2.95(d, 1H, J=11.2 Hz), 2.67(bs, 1H), 2.38(m, 1H), 2.11–1.94(m, 2H), 1.66–1.38(m, 8H), 1.26–1.01(m, 17H).

Mass(ESI): 717(M+1)

Example 11

Synthesis of 11-[(3RS,4RS)-7-hydroxy-3-(4-hydroxyphenyl)-3-methylthiochroman-4-yl]-2-(3,3,4,4,5,5,6,6,6-nonafluorohexyl)undecanoic acid

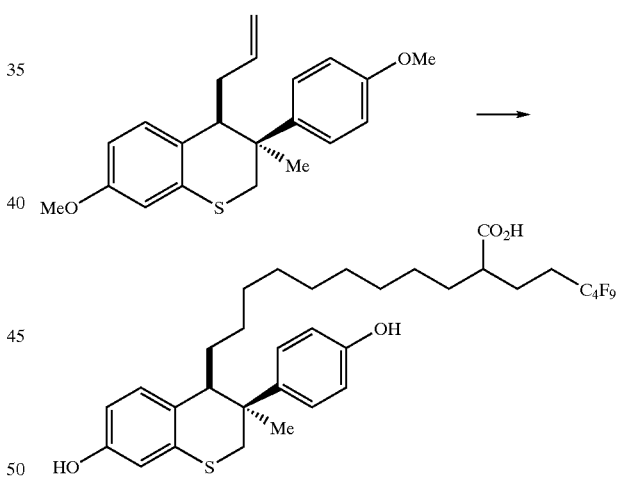

Starting with the allyl compound prepared in Example 8 and the ethyl 2-(3,3,4,4,5,5,6,6,6-nonafluorohexyl)-9-decenoate prepared in Example 6, a procedure analogous to that as shown in Example 8 was repeated to give 11-[(3RS,4RS)-7-hydroxy-3-(4-hydroxyphenyl)-3-methylthiochroman-4-yl]-2-(3,3,4,4,5,5,6,6,6-nonafluorohexyl)undecanoic acid.

$^1$H-NMR (300 MHz, CDCl$_3$): δ 7.24(d, 2H, J=9.2 Hz), 6.87(d, 1H, J=8.0 Hz), 6.83(d, 2H, J=9.6 Hz), 6.67(d, 1H, J=3.3 Hz), 6.50(dd, 1H, J=8.0 Hz, J$_2$=2.7 Hz), 3.62(d, 1H, J=11.2 Hz), 2.95(d, 1H, J=11.7 Hz), 2.71(m, 1H), 2.45(m, 1H), 2.17–2.05(m, 2H), 1.97–1.75(m, 2H), 1.67(m, 1H), 1.55(m, 1H), 1.25–1.00(m, 19H).

Mass(ESI): 703(M+1)

Example 12

Synthesis of 11-[(3RS,4RS)-7-hydroxy-3-(4-hydroxyphenyl)-3-methylthiochroman-4-yl]-2-(4,4,5,5,6,6,7,7,7-nonafluoroheptyl)undecanoic acid

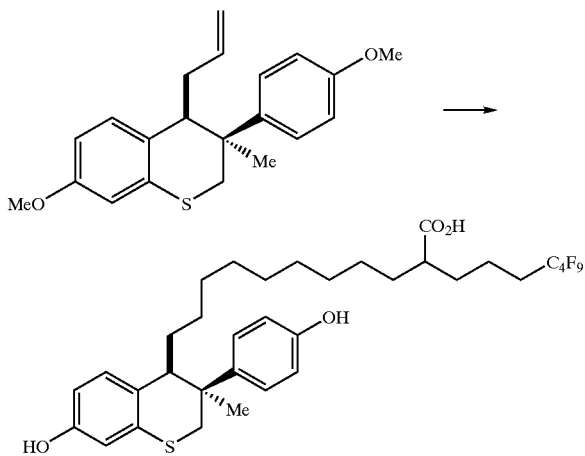

Starting with the allyl compound prepared in Example 8 and the ethyl 2-(4,4,5,5,6,6,7,7,7-nonafluoroheptyl)-9-decenoate prepared in Example 7, a procedure analogous to that as shown in Example 8 was repeated to give 11-[(3RS,4RS)-7-hydroxy-3-(4-hydroxyphenyl)-3-methylthiochroman-4-yl]-2-(4,4,5,5,6,6,7,7,7-nonafluoroheptyl)undecanoic acid.

$^1$H-NMR(300 MHz, CDCl$_3$): δ 7.23(d, 2H, J=8.7 Hz), 6.87(d, 1H, J=8.3 Hz), 6.83(d, 2H, J=8.7 Hz), 6.67(d, 1H, J=2.3 Hz), 6.50(dd, 1H, J$_1$=8.4 Hz, J$_2$=2.6 Hz), 3.62(d, 1H, J=11.6 Hz), 2.95(d, 1H, J=11.2 Hz), 2.70(m, 1H), 2.43(m, 1H), 2.15–1.97(m, 2H), 1.69–1.45(m, 6H), 1.28–1.07(m, 19H).

Mass(ESI): 717(M+1)

Example 13

Synthesis of 10-[(3RS,4RS)-7-hydroxy-3-(4-hydroxyphenyl)-3-methylchroman-4-yl]-2-(3,3,4,4,5,5,6,6,6-nonafluorohexyl)decanoic acid (Step 1)

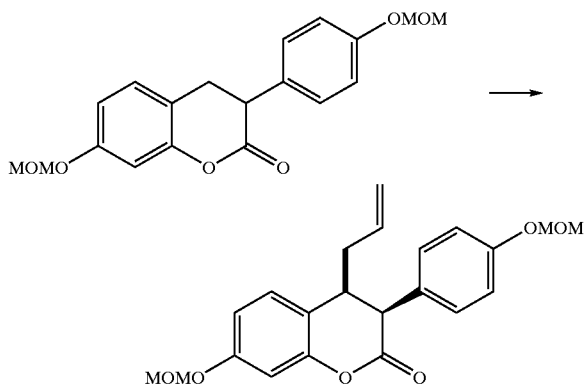

TBAF·n-H$_2$O (6 g) was azeotroped with toluene and ethanol (20 ml each) under reduced pressure to remove water and then concentrated twice with toluene (20 ml) under reduced pressure. The resulting light-yellow oil was dried using a vacuum pump to prepare anhydrous TBAF. A solution of this anhydrous TBAF in anhydrous dimethylformamide (80 ml) was added to a suspension of 7-methoxymethoxy-3-(4-methoxymethoxyphenyl)chromen-2-one (14.8 g) in anhydrous dimethylformamide (80 ml). To this suspension, a solution of HMPA (vacuum distilled while drying over calcium hydride, 27.1 ml) and allyltrimethylsilane (24.7 ml) in anhydrous dimethylformamide (80 ml) was added dropwise at room temperature over 15 minutes. The resulting red reaction mixture was stirred for 2 hours at room temperature and quenched with 1N hydrochloric acid (100 ml) in methanol (200 ml) on ice. The reaction mixture was extracted three times with ethyl acetate. The combined organic layers were washed three times with water and dried over magnesium sulfate. After concentration under reduced pressure, the resulting crude product was purified by silica gel column chromatography (Wakogel C-200, eluent: hexane/ethyl acetate=10/1→9/1) to give 7-methoxymethoxy-3-(4-methoxymethoxyphenyl)-4-(2-propenyl)chroman-2-one (14.1 g, Yield 85.0%) as a yellow oil.

$^1$H-NMR(279 MHz, CDCl$_3$): δ 7.23 (d,1H,J=8.6 Hz, Ar—H), 7.0–7.1 (m, 3H, Ar—H), 6.90 (d, 1H, 8.6 Hz, Ar—H), 6.7–6.9 (m, 2H, Ar—H), 5.5–5.9 (m, 1H, vinyl-H), 5.10, 5.15, 5.18 (each S,4H, OCH$_2$OMe), 4.8–5.2 (m, 2H, vinyl-H), 4.14 (d, 0.4H, J=5.6 Hz, C3-H), 4.03 (d, 0.6H, J=3.3 Hz, C3-H), 3.50, 3.48,3.43 (each s, 6H, OCH$_3$), 3.19 (td, 0.6H, J=6.9, 3.3 Hz, C4-H), 3.05–3.15 (m, 0.4H, C4-H), 2.1–2.5 (m, 2H, allylic-H).

(Step 2)

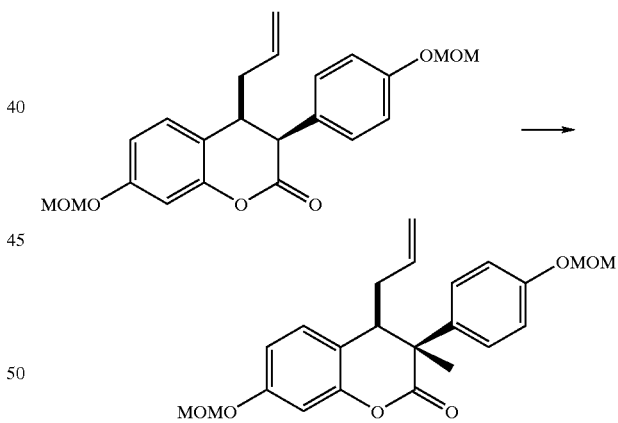

A 1M solution of lithium hexamethyl-disilazide in tetrahydrofuran (170 ml) was added dropwise to a solution of 7-methoxymethoxy-3-(4-methoxymethoxyphenyl)-4-(2-propenyl)chroman-2-one (32.70 g) in anhydrous tetrahydrofuran (400 ml) at –73° C. over 15 minutes under nitrogen atmosphere, followed by stirring for 30 minutes at –10° C. The reaction mixture was cooled to –75° C. and methyl iodide (10.6 ml) was added dropwise thereto over 10 minutes, followed by stirring for 10 minutes at –75° C., for 1 hour at –10° C. and then for 1 hour at 0° C. The reaction mixture was quenched with saturated aqueous ammonium chloride and partitioned between ethyl acetate and water. The organic layer was washed twice with water and dried over sodium sulfate. After concentration under reduced pressure, the resulting oil was purified by flash column chromatography (silica gel: Merck Kieselgel 60, eluent: hexane/ethyl acetate=9/1) to give (3RS,4RS)-7-methoxymethoxy-3-(4-methoxymethoxyphenyl)-3-methyl-4-(2-propenyl)chroman-2-one (30.74 g, Yield 90.8%) as a yellow oil.

$^1$H-NMR(270 MHz, CDCl$_3$): δ 7.44 (d, 2H, J=8.6 Hz, Ar—H), 7.00–7.05 (m, 3H, Ar—H), 6.75–6.80 (m, 2H, Ar—H), 5.40–5.65 (m, 1H, vinyl-H), 5.18, 5.17 (each S,4H, OCH$_2$Me), 4.92 (d, 1H, J=10.2 Hz, vinyl-H), 4.79 (d, 1H, J=17.2 Hz, vinyl-H), 3.50, 3.49 (each s, 6H, OCH$_3$), 2.84 (dd, 1H, J=9.9, 3 Hz, C4-H), 2.15–2.30 (m, 1H, allylic-H), 1.90–2.05 (m, 1H, allylic-H), 1.61 (s, 3H, C3-CH$_3$).

(Step 3)

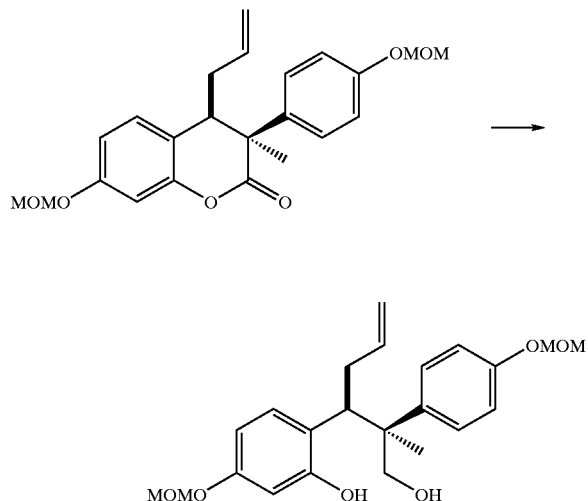

A solution of (3RS,4RS)-7-methoxymethoxy-3-(4-methoxymethoxyphenyl)-3-methyl-4-(2-propenyl)chroman-2-one (6.91 g) in anhydrous tetrahydrofuran (26 ml) was added dropwise to an ice-cold suspension of lithium aluminum hydride (1.65 g) in anhydrous tetrahydrofuran (50 ml) over 20 minutes under nitrogen atmosphere, and the reaction mixture was then stirred on ice for 50 minutes. Ethyl acetate (20 ml) and saturated aqueous ammonium chloride (20 ml) were added to stop the reaction, followed by stirring for 1 hour at room temperature. The reaction mixture was filtered through cellite and the resulting filtrate was extracted twice with ethyl acetate. The combined organic layers were washed with saturated aqueous ammonium chloride, dried over magnesium sulfate and then concentrated under reduced pressure to give (2RS,3RS)-3-(2-hydroxy-4-methoxymethoxyphenyl)-2-(4-methoxymethoxyphenyl)-2-methyl-5-hexen-1-ol (6.94 g, Yield 99.4%) as a crude product, which was then used for the subsequent reaction without further purification.

$^1$H-NMR(270 MHz, CDCl$_3$): δ 7.3–7.6 (bs, 1H, Ar—OH), 6.9–7.1 (m, 4H, Ar—H), 6.57 (d, 1H, J=2.3 Hz, Ar—H), 6.37 (dd, 1H, J=8.6, 2.3 Hz, Ar—H), 6.05–6.25 (d, 1H, Ar—H), 6.3–6.5 (m, 1H, vinyl-H), 5.18 (s, 2H, OCH$_2$OMe), 5.12 (d, 2H, J=6.9 Hz, OCH$_2$OMe), 4.84 (d, 1H, J=17.2 Hz, vinyl-H), 4.75 (d, 1H, J=10.2 Hz, vinyl-H), 3.92 (d, 1H, J=9.9 Hz, C1-H), 3.49, 3.50 (each s, 6H, OCH$_3$), 3.4–3.5 (m, 1H, C1-H), 3.25–3.35 (m, 1H, C3-H), 2.8–3.0 (d, 1H, OH), 2.5–2.7 (m, 1H, C4-H), 1.95–2.2 (m, 1H, C4-H), 1.63 (s, 3H, C3-CH$_3$).

(Step 4)

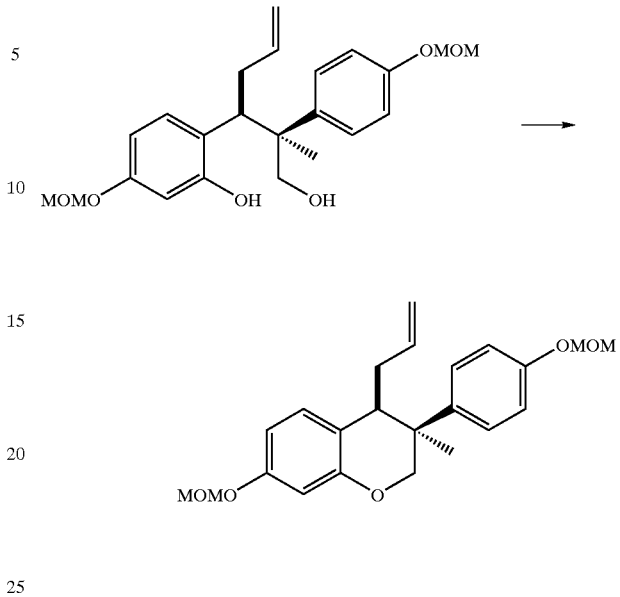

Diethyl azodicarboxylate (5.94 ml) was added dropwise to an ice-cold solution of (2RS,3RS)-3-(2-hydroxy-4-methoxymethoxyphenyl)-2-(4-methoxymethoxyphenyl)-2-methyl-5-hexen-1-ol (6.9 g) and triphenylphosphine (11.24 g) in anhydrous 1,4-dioxane (120 ml) over 25 minutes under nitrogen atmosphere. The reaction mixture was stirred for 20 minutes at room temperature. Water was added to the reaction mixture, which was then extracted twice with ethyl acetate. The combined organic layers were dried over magnesium sulfate and concentrated to give a crude product, which was then purified by flash column chromatography (silica gel: Merck Kieselgel 60, eluent: hexane/ethyl acetate=100/1→20/1→9/1) to give (3RS,4RS)-7-methoxymethoxy-3-(4-methoxymethoxyphenyl)-3-methyl-4-(2-propenyl)chroman (6.5 g, Yield 98.6%) as a colorless oil.

$^1$H-NMR(270 MHz, CDCl$_3$): δ7.03, 7.15 (each d, 4H, J=8.9 Hz, Ar—H), 6.96 (d, 1H, J=7.9 Hz, Ar—H), 6.5–6.6 (m, 2H, Ar—H), 5.5–5.7 (m, 1H, vinyl-H), 5.18 (s, 2H, OCH$_2$OMe), 5.14 (d, 2H, J=6.9 Hz, OCH$_2$OMe), 4.86 (dd, 1H, J=10.2, 1.3 Hz, vinyl-H), 4.70 (dd, 1H, J=17.2, 1.3 Hz, vinyl-H), 4.52 (d, 1H, J=10.2 Hz, C2-H), 4.26 (dd, 1H, J=10.6, 2.0 Hz, C2-H), 3.49, 3.50 (each s, 6H, OCH$_3$), 3.75–3.85 (m, 1H, C4-H), 2.0–2.1 (m, 1H, allylic-H), 1.8–1.9 (m, 1H, allylic-H), 1.29 (s, 3H, C3-CH$_3$).

(Step 5)

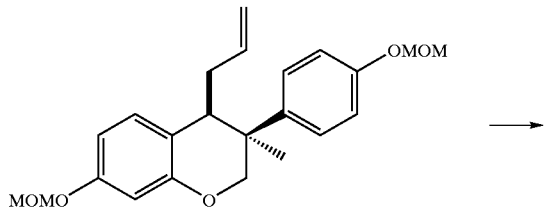

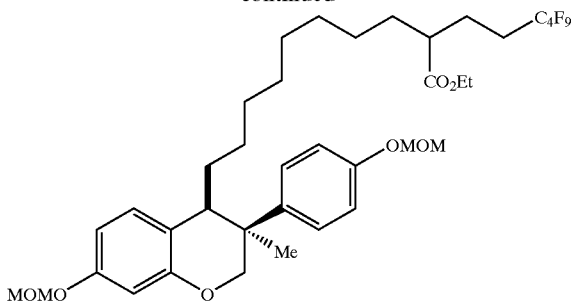

Benzylidene-bis(tricyclohexylphosphine) dichlororuthenium (191 mg, 0.232 mmol) was added to a dichloromethane (30 ml) solution of (3RS,4RS)-7-methoxy-methoxy-3-(4-methoxymethoxyphenyl)-3-methyl-4-(2-propenyl)-chroman (893 mg) and the ethyl 2-(3,3,4,4,5,5,6,6,6-nonafluorohexyl)-8-nonenoate prepared in Example 3 (2.0 g, 4.647 mmol), followed by heating under reflux for 12 hours. After distilling off the solvent, the residue was purified by silica gel column chromatography (eluent: ethyl acetate/hexane=1/30→1/20) to give the desired olefin (1.33 g, Yield 73%) as an oil.

10% Palladium carbon (130 mg) was added to a solution of the thus prepared olefin (1.33 g, 1.652 mmol) in ethyl acetate (50 ml) followed by stirring for 4 hours at room temperature under hydrogen atmosphere. The reaction mixture was filtered and the resulting filtrate was concentrated under reduced pressure to give ethyl 10-[(3RS,4RS)-7-(methoxymethoxy)-3-(4-methoxymethoxyphenyl)-3-methylchroman-4-yl]-2-(3,3,4,4,5,5,6,6,6-nonafluorohexyl) decanoate (1.33 g, calculated) as a colorless oil.

$^1$H-NMR (300 MHz, CDCl$_3$): δ 7.13 (d, 2H, J=8.7 Hz), 7.03 (d, 2H, J=9.0 Hz), 6.94 (m, 1H), 6.57–6.54 (m, 2H), 5.18 (s, 2H), 5.14 (s, 2H), 4.52 (d, 1H, J=10.2 Hz), 4.25 (dd, 1H, J$_1$=10.2 Hz, J$_2$=1.5 Hz), 4.15 (q, 2H, J=7.2 Hz), 3.49 (s, 6H), 2.63 (m, 1H), 2.36 (m, 1H), 2.10–1.70 (m, 4H), 1.60–1.13 (m, 22H).

(Step 6)

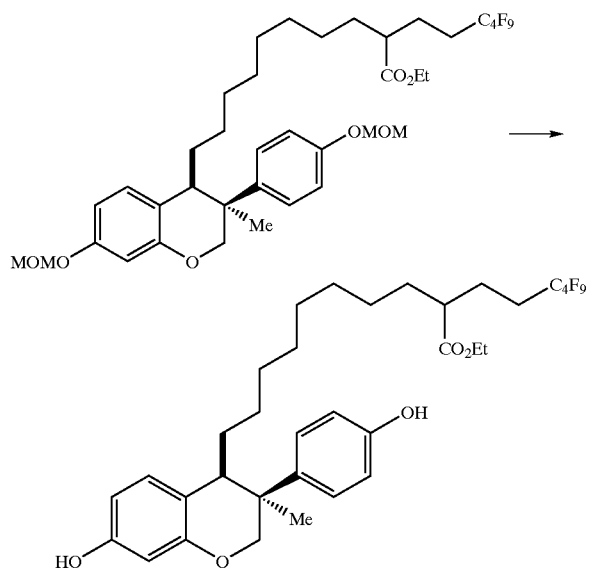

Concentrated hydrochloric acid (10 drops) was added to a solution of ethyl 10-[(3RS,4RS)-7-(methoxymethoxy)-3-(4-methoxymethoxyphenyl)-3-methylchroman-4-yl]-2-(3,3,4,4,5,6,6,6-nonafluorohexyl)decanoate (1.33 g, 1.686 mmol) in methanol (15 ml) followed by stirring for 4 hours at 50° C. The reaction mixture was neutralized with aqueous sodium bicarbonate and then concentrated under reduced pressure. Water was added to the residue, which was then extracted with ethyl acetate. The organic layer was washed with saturated aqueous sodium chloride and dried over anhydrous magnesium sulfate. After distilling off the solvent, the residue was purified by silica gel column chromatography (eluent: ethyl acetate/hexane=1/4) to give ethyl 10-[(3RS,4RS)-7-hydroxy-3-(4-hydroxyphenyl)-3-methylchroman-4-yl]-2-(3,3,4,4,5,5,6,6,6-nonafluorohexyl) decanoate (1.10 g, Yield 93%) as a colorless oil.

$^1$H-NMR (300 MHz, CDCl$_3$): δ 7.07 (d, 2H, J=8.7 Hz), 6.90 (d, 1H, J=7.5 Hz), 6.82 (d, 2H, J=8.7 Hz), 6.39–6.35 (m, 2H), 5.58 (m, 1H), 4.84 (bs, 1H), 4.50 (d, 1H, J=10.6 Hz), 4.24 (d, 1H, J=10.6 Hz), 4.22 (q, 2H, J=8.7 Hz), 2.59 (bs, 1H), 2.40 (m, 1H), 2.38–1.43 (m, 6H), 1.27–1.00 (m, 20H).

Mass (ESI): 701(M+1)

(Step 7)

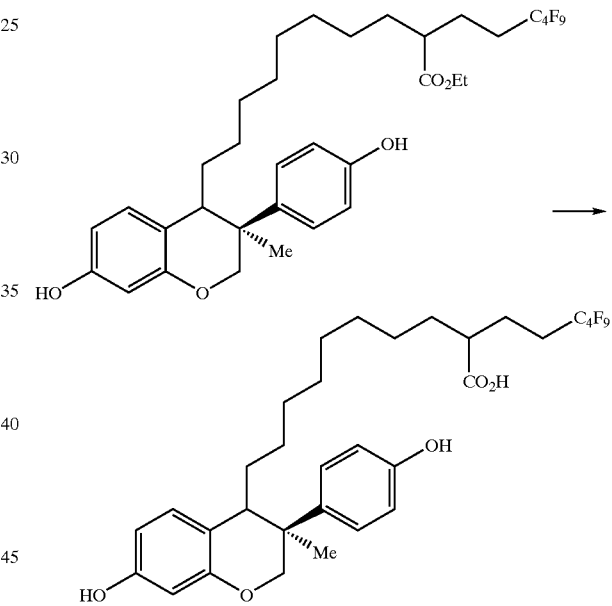

Ethyl 10-[(3RS,4RS)-7-hydroxy-3-(4-hydroxyphenyl)-3-methylchroman-4-yl]-2-(3,3,4,4,5,5,6,6,6-nonafluorohexyl) decanoate (1.10 g, 1.570 mmol) and potassium hydroxide (880 mg, 15.70 mmol) were added to a methanol/water mixture (2:1, 15 ml), followed by heating under reflux for 4 hours. After the reaction mixture was neutralized with 1N hydrochloric acid, the solvent was distilled off under reduced pressure. The residue was diluted with water, adjusted to pH 2–3 with 1N hydrochloric acid, and then extracted with ethyl acetate. The organic layer was washed with saturated aqueous sodium chloride and dried over anhydrous magnesium sulfate. After distilling off the solvent, the residue was purified by silica gel column chromatography (eluent: ethyl acetate/hexane=1/4) to give 10-[(3RS,4RS)-7-hydroxy-3-(4-hydroxyphenyl)-3-methylchroman-4-yl]-2-(3,3,4,4,5,5,6,6,6-nonafluorohexyl) decanoic acid (852 mg, Yield 81%) as a colorless foam.

$^1$H-NMR (300 MHz, CDCl$_3$): δ 7.08 (d, 2H, J=8.6 Hz), 6.90 (d, 1H, J=8.6 Hz), 6.83 (d, 2H, J=8.6 Hz), 6.38 (m, 2H), 4.51 (d, 1H, J=10.2 Hz), 4.23 (d, 1H, J=9.8 Hz), 2.58 (m, 1H), 2.45 (m, 1H), 2.12 (m, 2H), 2.00–1.72 (m, 2H), 1.70–1.40 (m, 2H), 1.25–1.00 (m, 17H).

Mass (ESI): 673 (M+1).

Example 14

Synthesis of 11-[(3RS,4RS)-7-hydroxy-3-(4-hydroxyphenyl)-3-methylchroman-4-yl]-2-(3,3,4,4,5,5,6,6,6-nonafluorohexyl)undecanoic acid

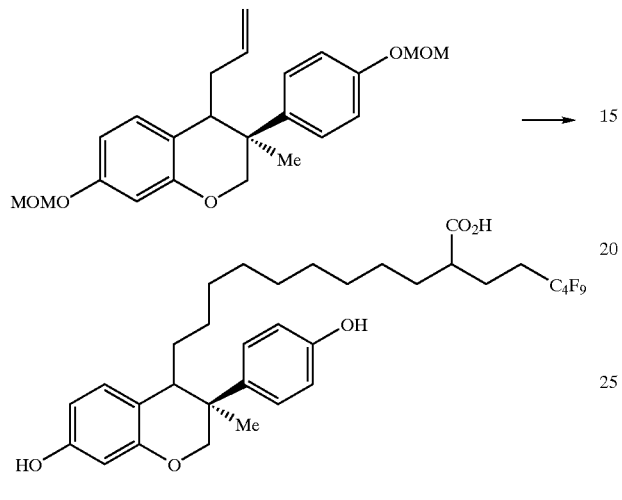

Starting with the allyl compound prepared in Example 13 and the ethyl 2-(3,3,4,4,5,5,6,6,6-nonafluorohexyl)-9-decenoate prepared in Example 6, a procedure analogous to that as shown in Example 13 was repeated to give 11-[(3RS,4RS)-7-hydroxy-3-(4-hydroxyphenyl)-3-methylchroman-4-yl]-2-(3,3,4,4,5,5,6,6,6-nonafluorohexyl)undecanoic acid.

$^1$H-NMR (300 MHz, CDCl$_3$): δ 7.18 (d, 2H), 6.90 (d, 1H), 6.82 (d, 2H), 6.38 (d, 1H), 6.35 (s, 1H), 4.5 (d, 1H), 4.26 (d, 1H), 2.59 (d, 1H), 2.46 (m, 1H), 2.12 (m, 2H), 1.85–1.81 (m, 2H), 1.66 (m, 1H), 1.51 (m, 1H), 1.28–1.07 (m, 19H), Mass(ESI): 687 (M+1).

Example 15

Synthesis of 10-[(3RS,4RS)-7-hydroxy-3-(4-hydroxyphenyl)-3-methylchroman-4-yl]-2-(4,4,5,5,6,6,7,7,7-nonafluoroheptyl)decanoic acid

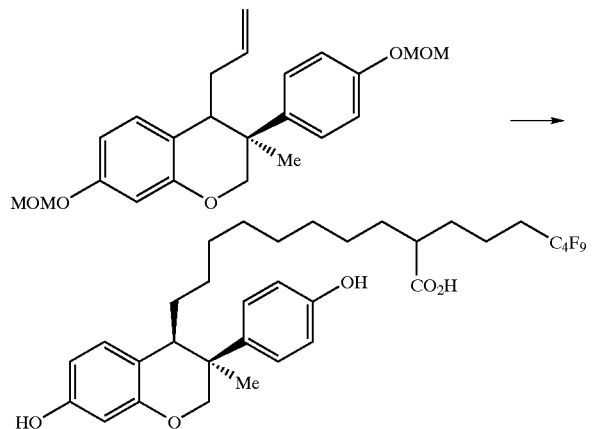

Starting with the allyl compound prepared in Example 13 and the ethyl 2-(4,4,5,5,6,6,7,7,7-nonafluoroheptyl)-8-nonenoate prepared in Example 4, a procedure analogous to that as shown in Example 13 was repeated to give 10-[(3RS,4RS)-7-hydroxy-3-(4-hydroxyphenyl)-3-methylchroman-4-yl]-2-(4,4,5,5,6,6,7,7,7-nonafluoroheptyl)decanoic acid.

$^1$H-NMR(300 MHz, CDCl$_3$): δ 7.10(d, J=8.7 Hz, 2H, Ar—H), 6.95(d, J=8.9 Hz, 1H, Ar—H), 6.82(d, J=8.5 Hz, 2H, Ar—H), 6.33–6.36(m, 2H, Ar—H), 4.50(d, J=10.4 Hz, 1H, OCH2), 4.28(d, J=10.2 Hz, 1H, OCH2), 2.59–2.70(m, 1H, Ar—CH), 2.23–2.51(m, 1H, CHCO$_2$H), 1.82–2.15(m, 2H, CH$_2$CF$_2$), 0.92–1.85(m, 23H, alkyl-H).

Mass(ESI): 687(M+1)

Example 16

Synthesis of 11-[(3RS,4RS)-7-hydroxy-3-(4-hydroxyphenyl)-3-methylchroman-4-yl]-2-(4,4,5,5,6,6,7,7,7-nonafluoroheptyl)undecanoic acid

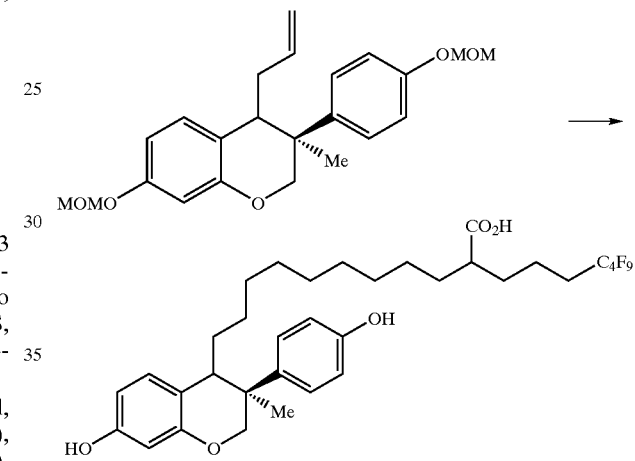

Starting with the allyl compound prepared in Example 13 and the ethyl 2-(4,4,5,5,6,6,7,7,7-nonafluoroheptyl)-9-decenoate prepared in Example 7, a procedure analogous to that as shown in Example 13 was repeated to give 11-[(3RS,4RS)-7-hydroxy-3-(4-hydroxyphenyl)-3-methylchroman-4-yl]-2-(4,4,5,5,6,6,7,7,7-nonafluoroheptyl)undecanoic acid.

$^1$H-NMR(270 MHz, CDCl$_3$): δ 7.05 (d, J=8.6 Hz, 2H), 6.87 (d, J=8.9 Hz, 1H, C5-CH), 6.80 (d, J=8.6 Hz, 2H), 6.4–6.3 (m, 2H, C6-CH and C8-CH), 4.48 (d, J=10.2 Hz, 1H, C2-CH$_2$), 4.21 (d, J=10.2 Hz, 1H, C2-CH$_2$), 2.7–2.5 (m, 1H, C4-CH), 2.5–2.3 (m, 1H), 2.2–1.9 (m, 2H), 1.8–1.0 (m, 28H).

Example 17

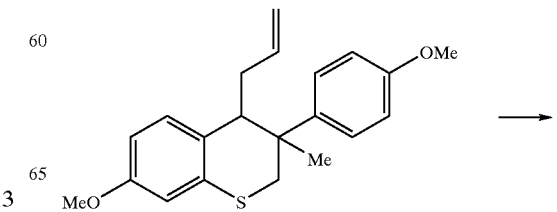

-continued

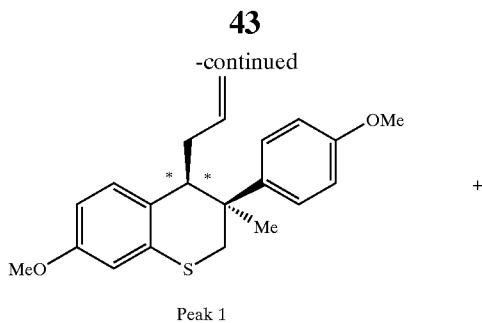

Peak 1

Peak 2

Optical resolution of the (3RS,4RS)-7-methoxy-3-(4-methoxyphenyl)-3-methyl-4-(2-propenyl)thiochroman prepared in Example 8 was carried out using a chiral column (CHIRALCEL OD) to give (3S,4S)-7-methoxy-3-(4-methoxyphenyl)-3-methyl-4-(2-propenyl)thiochroman as Peak 1 and (3R,4R)-7-methoxy-3-(4-methoxyphenyl)-3-methyl-4-(2-propenyl)thiochroman as Peak 2.

Peaks 1 and 2 were detected at retention times of 4.3 and 5.1 minutes, respectively, under the following conditions:

Column used: CHIRALCEL OD (0.46 cm ID×25 cm L)
Mobile phase: hexane/isopropanol=90/10 (v/v)
Flow rate: 1.0 ml/min
Column temperature: 40° C.
Detection wavelength: 254 nm Example 18

Synthesis of 10-[(3S,4S)-7-hydroxy-3-(4-hydroxyphenyl)-3-methylthiochroman-4-yl]-2-(3,3,4,4,5,5,6,6,6-nonafluorohexyl)decanoic acid

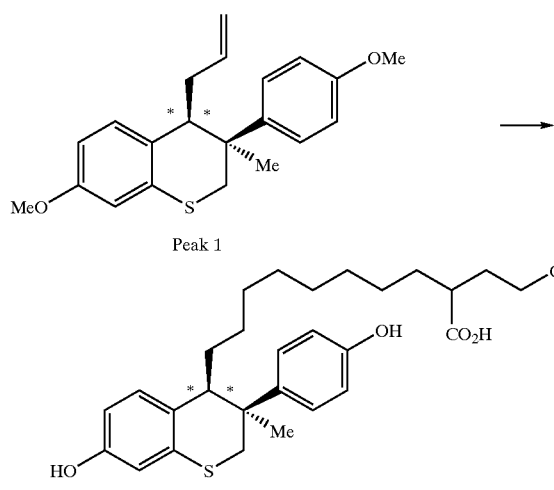

Peak 1

Starting with the (3S,4S)-7-methoxy-3-(4-methoxyphenyl)-3-methyl-4-(2-propenyl)thiochroman resolved as Peak 1 in Example 17 and the ethyl 2-(3,3,4,4, 5,5,6,6,6-nonafluorohexyl)-8-nonenoate prepared in Example 3, a procedure analogous to that as shown in Example 8 was repeated to give 10-[(3S,4S)-7-hydroxy-3-(4-hydroxyphenyl)-3-methylthiochroman-4-yl]-2-(3,3,4,4, 5,5,6,6,6-nonafluorohexyl)decanoic acid.

This compound provided the same NMR data as shown in Example 8.

Example 19

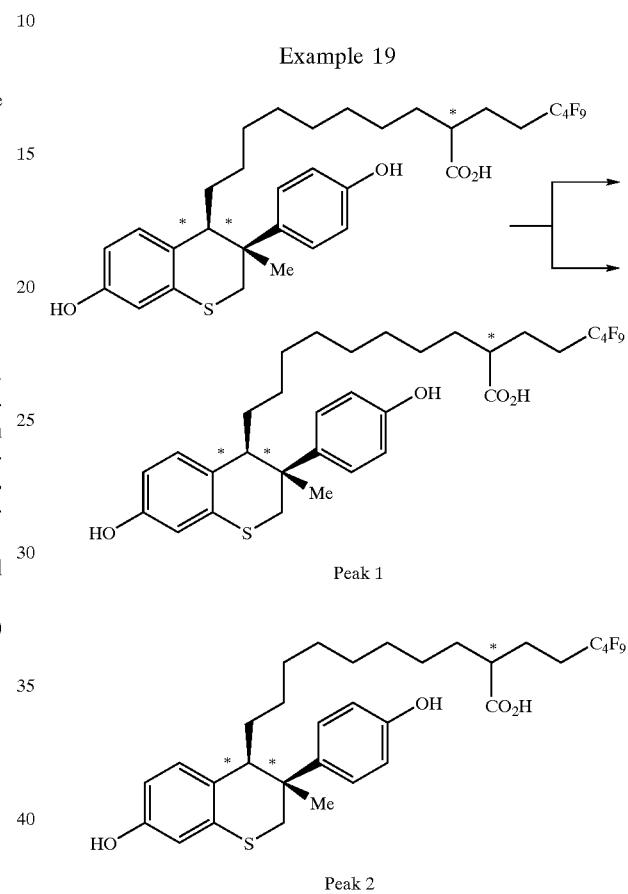

Peak 1

Peak 2

Optical resolution of the 10-[(3S,4S)-7-hydroxy-3-(4-hydroxyphenyl)-3-methylthiochroman-4-yl]-2-(3,3,4,4,5,5,6,6,6-nonafluorohexyl)decanoic acid prepared in Example 18 was carried out using a chiral column (CHIRALPAK AD) to give optically active isomers, each having chiral carbons at positions 3 and 4 and at α-position to the carboxyl group.

Each isomer provided the same NMR data as shown in Example 8.

Peaks 1 and 2 were detected at retention times of 32 and 38 minutes, respectively, under the following conditions:

Column used: CHIRALPAK AD (0.46 cm ID×25 cm L)
Mobile phase: hexane/isopropanol/acetic acid=90/10/0.2 (v/v/v)
Flow rate: 1.0 ml/min
Column temperature: 40° C.
Detection wavelength: 280 nm

Example 20

Synthesis of 10-[(3R,4R)-7-hydroxy-3-(4-hydroxyphenyl)-3-methylthiochroman-4-yl]-2-(3,3,4,4,5,5,6,6,6-nonafluorohexyl)decanoic acid

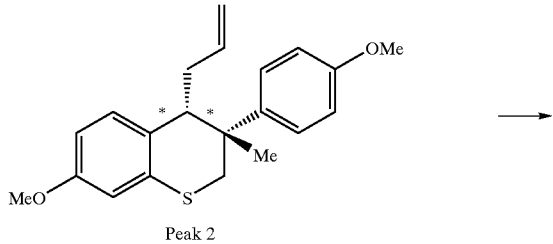

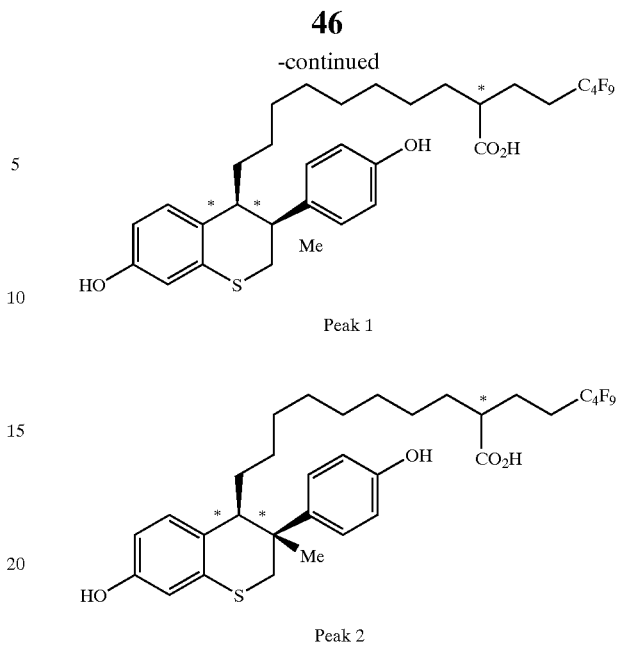

Peak 1

Peak 2

Starting with the (3R,4R)-7-methoxy-3-(4-methoxyphenyl)-3-methyl-4-(2-propenyl)thiochroman resolved as Peak 2 in Example 17 and the ethyl 2-(3,3,4,4,5,5,6,6,6-nonafluorohexyl)-8-nonenoate prepared in Example 3, a procedure analogous to that as shown in Example 8 was repeated to give 10-[(3R,4R)-7-hydroxy-3-(4-hydroxyphenyl)-3-methylthiochroman-4-yl]-2-(3,3,4,4,5,5,6,6,6-nonafluorohexyl)decanoic acid.

This compound provided the same NMR data as shown in Example 8.

Example 21

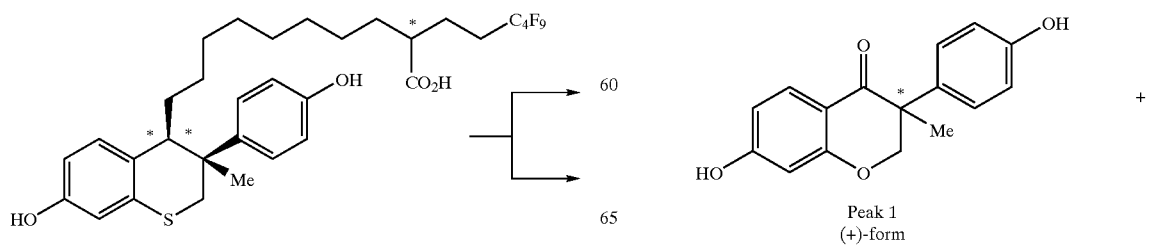

Optical resolution of the 10-[(3R,4R)-7-hydroxy-3-(4-hydroxyphenyl)-3-methylthiochroman-4-yl]-2-(3,3,4,4,5,5,6,6,6-nonafluorohexyl)decanoic acid prepared in Example 20 was carried out using a chiral column (CHIRALPAK AD) to give optically active isomers, each having chiral carbons at positions 3 and 4 and at α-position to the carboxyl group.

Each isomer provided the same NMR data as shown in Example 8.

Peaks 1 and 2 were detected at retention times of 30 and 34 minutes, respectively, under the following conditions:

Column used: CHIRALPAK AD (0.46 cm ID×25 cm L)
Mobile phase: hexane/isopropanol/acetic acid=90/10/0.2 (v/v/v)
Flow rate: 0.8 ml/min
Column temperature: 40° C.
Detection wavelength: 280 nm

Example 22

Optical resolution of 7-hydroxy-3-(4-hydroxyphenyl)-3-methylchroman-4-one

Peak 1
(+)-form

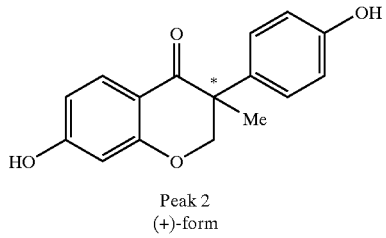

Peak 2
(+)-form

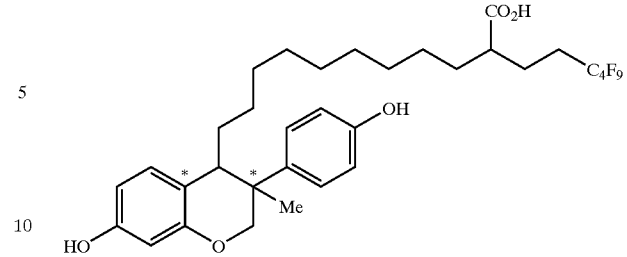

Optical resolution of (±)-7-hydroxy-3-(4-hydroxyphenyl)-3-methylchroman-4-one was carried out using a chiral column (CHIRALCEL OD) to give (+)-7-hydroxy-3-(4-hydroxyphenyl)-3-mehtylchroman-4-one as Peak 1 and (−)-7-hydroxy-3-(4-hydroxyphenyl)-3-mehtylchroman-4-one as Peak 2.

Peaks 1 and 2 were detected at retention times of 7.2 and 10.2 minutes, respectively, under the following conditions:

Column used: CHIRALCEL OD (0.46 cm ID×25 cm L)

Mobile phase: hexane/isopropanol=80/20 (v/v)

Flow rate: 1.0 ml/min

Column temperature: 40° C.

Detection wavelength: 290 nm

Example 23

Synthesis of 11-[7-hydroxy-3-(4-hydroxyphenyl)-3-methylchroman-4-yl]-2-(3,3,4,4,5,5,6,6,6-nonafluorohexyl)undecanoic acid having chiral carbons at positions 3 and 4

(Step 1)

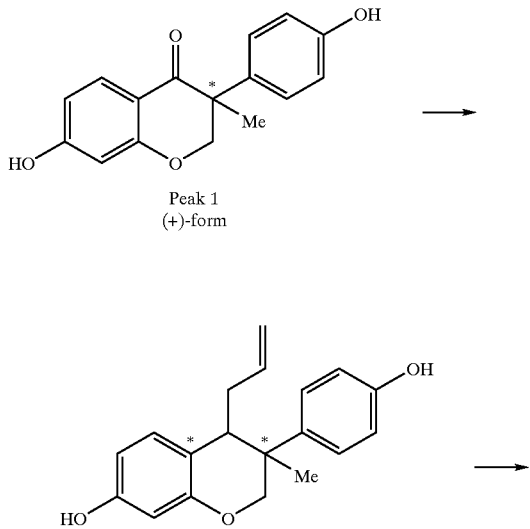

The (+)-7-hydroxy-3-(4-hydroxyphenyl)-3-methylchroman-4-one resolved as Peak 1 in Example 22 (2.0 g, 7.40 mmol) was dissolved in anhydrous tetrahydrofuran (30 ml) and then cooled to −78° C. To this solution, a solution of diisobutylaluminum hydride in toluene (1N, 22.94 ml, 22.94 mmol) was slowly added dropwise, and the resulting mixture was stirred for 35 minutes at −78° C. Methanol (1 ml) was added to the reaction mixture at −78° C., which was then warmed to 0° C. and saturated aqueous ammonium chloride (5 ml) and concentrated hydrochloric acid (7 ml) were added to the mixture followed by stirring for 30 minutes. The reaction mixture was extracted twice with ethyl acetate. The combined organic layers were washed with water and saturated aqueous sodium chloride, and then dried over anhydrous magnesium sulfate. After distilling off the solvent, zinc iodide (2.55 g, 7.98 mmol) was added to a suspension of the residue and allyltrimethylsilane (5.3 ml, 33.2 mmol) in 1,2-dichloroethane (80 ml) followed by stirring for 12 hours at room temperature. Saturated aqueous ammonium chloride (15 ml), methanol (10 ml) and concentrated hydrochloric acid (10 ml) were added to the reaction mixture, followed by stirring for 30 minutes. The reaction mixture was extracted twice with dichloromethane. The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/4) to give optically active 7-hydroxy-3-(4-hydroxyphenyl)-3-methyl-4-(2-propenyl)chroman (cis-configuration, 859 mg, Yield 44%).

$^1$H-NMR(270 MHz, CDCl$_3$): δ 7.10 (d, J=8.6 Hz, 2H, Ar—H), 6.91 (d, J=8.6 Hz, 1H, Ar—H), 6.84 (d, J=8.6 Hz, 2H, Ar—H), 6.3–6.4 (m, 2H, Ar—H), 6.5–6.7 (m, 1H, vinyl-H), 4.60–5.00 (br, 2H, OH), 4.86 (d, J=10.2 Hz, 1H, vinyl-H), 4.69 (d, J=16.8 Hz, 1H, vinyl-H), 4.51 (d, J=10.6 Hz, 1H, C2-H), 4.24 (dd, J=10.6, 2.0 Hz, C2-H), 2.7–2.8 (m, 1H, C4-H), 2.0–2.15 (m, 1H, allylic-H), 1.75–1.9 (m, 1H, allylic-H), 1.28 (s, 3H, C3-CH$_3$).

Starting with the optically active 7-hydroxy-3-(4-hydroxyphenyl)-3-methyl-4-(2-propenyl)chroman prepared in Step 1, a procedure analogous to that as shown in Example 13 was repeated without protection of hydroxyl groups to give 11-[7-hydroxy-3-(4-hydroxyphenyl)-3-methylchroman-4-yl]-2-(3,3,4,4,5,5,6,6,6-nonafluorohexyl) undecanoic acid with a cis-configuration having chiral carbons at positions 3 and 4.

This compound provided the same NMR data as shown in Example 14.

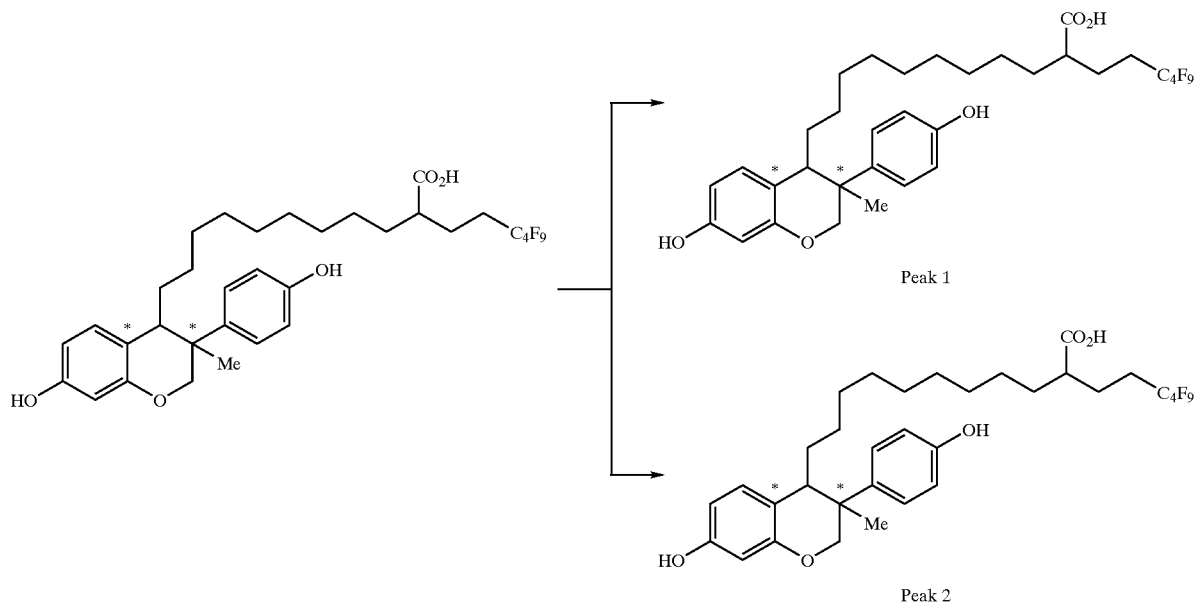

Peak 1

Peak 2

The 11-[7-hydroxy-3-(4-hydroxyphenyl)-3-methylchroman-4-yl]-2-(3,3,4,4,5,5,6,6,6-nonafluorohexyl)undecanoic acid having chiral carbons at positions 3 and 4 which was prepared in Example 23 was optically resolved at α-position to the carboxyl group using a chiral column (CHIRALPAK AD) to give optically active isomers, each having chiral carbons at positions 3 and 4 and at α-position to the carboxyl group.

Each isomer provided the same NMR data as shown in Example 14.

Peaks 1 and 2 were detected at retention times of 17.5 and 20.7 minutes, respectively, under the following conditions:

Column used: CHIRALPAK AD (0.46 cm ID×25 cm L)

Mobile phase: hexane/isopropanol/acetic acid=90/10/0.1 (v/v/v)

Flow rate: 1.0 ml/min

Column temperature: 40° C.

Detection wavelength: 254 nm

Example 25

Synthesis of 11-[7-hydroxy-3-(4-hydroxyphenyl)-3-methylchroman-4-yl]-2-(3,3,4,4,5,5,6,6,6-nonafluorohexyl)undecanoic acid having chiral carbons at positions 3 and 4

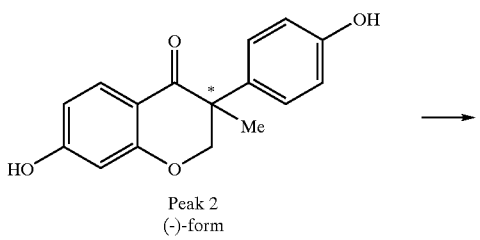

Peak 2
(−)-form

Example 24

-continued

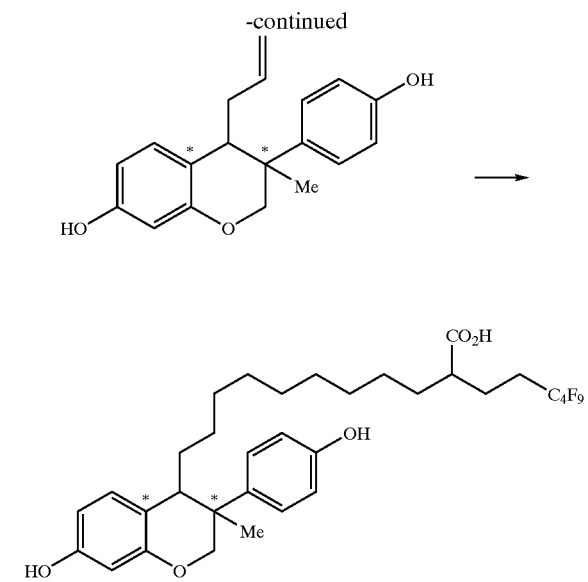

Starting with the (−)-7-hydroxy-3-(4-hydroxyphenyl)-3-mehtylchroman-4-one resolved as Peak 2 in Example 22, a procedure analogous to that as shown in Example 23 was repeated to give 11-[7-hydroxy-3-(4-hydroxyphenyl)-3-methylchroman-4-yl]-2-(3,3,4,4,5,5,6,6,6-nonafluorohexyl)undecanoic acid with a cis-configuration having chiral carbons at positions 3 and 4.

This compound provided the same NMR data as shown in Example 14.

Example 26

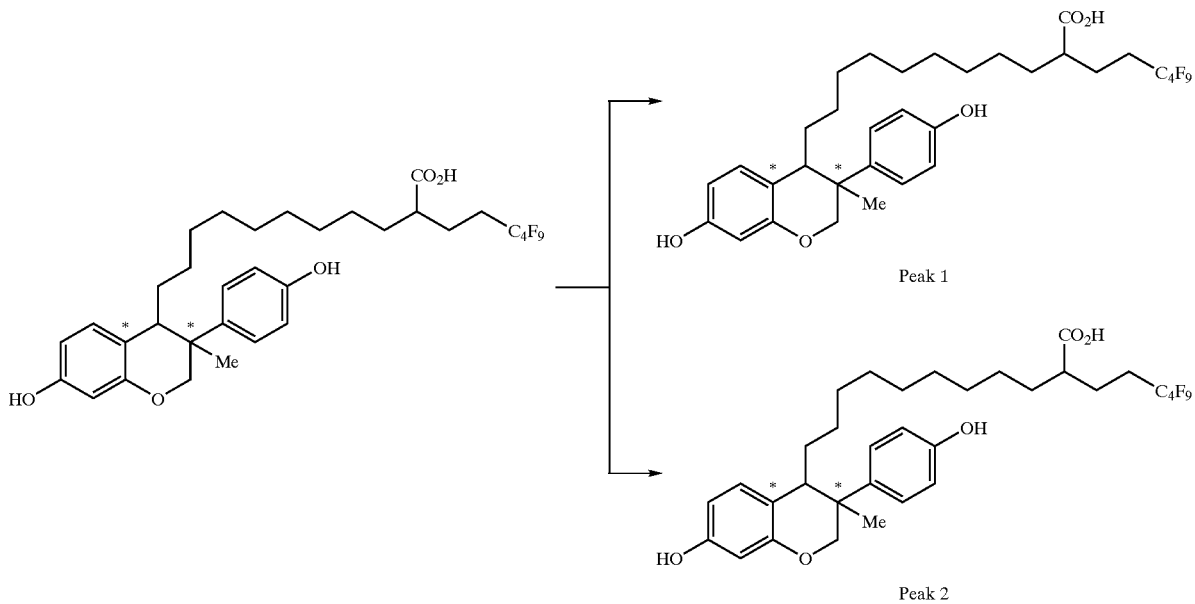

The 11-[7-hydroxy-3-(4-hydroxyphenyl)-3-methylchroman-4-yl]-2-(3,3,4,4,5,5,6,6,6-nonafluorohexyl)undecanoic acid having chiral carbons at positions 3 and 4 which was prepared in Example 25 was optically resolved at α-position to the carboxyl group using a chiral column (CHIRALPAK AD) to give optically active isomers, each having chiral carbons at positions 3 and 4 and at α-position to the carboxyl group.

Each isomer provided the same NMR data as shown in Example 14.

Peaks 1 and 2 were detected at retention times of 8.4 and 10.8 minutes, respectively, under the following conditions:

Column used: CHIRALPAK AD (0.46 cm ID×25 cm L)
Mobile phase: hexane/isopropanol/acetic acid=80/20/0.1 (v/v/v)
Flow rate: 1.0 ml/min
Column temperature: 40° C.
Detection wavelength: 254 nm

Example 27

Synthesis of sodium 10-[(3RS,4RS)-7-hydroxy-3-(4-hydroxyphenyl)-3-methylthiochroman-4-yl]-2-(3,3,4,4,5,5,6,6,6-nonafluorohexyl)decanoate

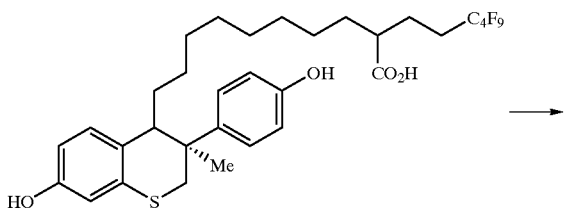

A solution of sodium methoxide in methanol (1.0 mol/l, 0.145 ml, 0.145 mmol) was added to a methanol (1 ml) solution of the 10-[(3RS,4RS)-7-hydroxy-3-(4-hydroxyphenyl)-3-methylthiochroman-4-yl]-2-(3,3,4,4,5,5,6,6,6-nonafluorohexyl)decanoic acid prepared in Example 8 (100 mg, 0.145 mmol), followed by stirring for 2 hours at room temperature. After addition of ethyl ether, the reaction mixture was evaporated under reduced pressure to remove the solvent, thereby giving sodium 10-[(3RS,4RS)-7-hydroxy-3-(4-hydroxyphenyl)-3-methylthiochroman-4-yl]-2-(3,3,4,4,5,5,6,6,6-nonafluorohexyl)decanoate.

$^1$H-NMR(270 MHz, CD$_3$OD): δ 7.13 (d, J=8.9 Hz, 2H), 6.74 (d, J=8.3 Hz, 1H, C5-H), 6.69 (d, J=8.6 Hz, 2H), 6.45 (d, J=2.6 Hz, 1H, C8-H), 6.34 (dd, J=8.3, 2.6 Hz, 1H, C6-H), 3.52 (d, J=11.6 Hz, 1H, C2-H$_2$), 2.84 (d, J=11.6 Hz, 1H, C2-CH$_2$), 2.7–2.6 (m, 1H, C4-H), 2.2–2.0 (m, 3H), 1.8–1.4 (m, 3H), 1.3–0.9 (m, 18H).

Example 28

Synthesis of sodium 11-[(3RS,4RS)-7-hydroxy-3-(4-hydroxyphenyl)-3-methylchroman-4-yl]-2-(3,3,4,4,5,5,6,6,6-nonafluorohexyl)undecanoate

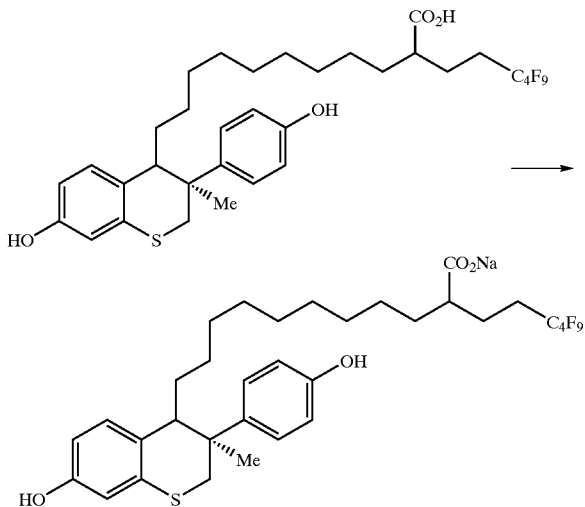

Starting with the 11-[(3RS,4RS)-7-hydroxy-3-(4-hydroxyphenyl)-3-methylchroman-4-yl]-2-(3,3,4,4,5,5,6,6,6-nonafluorohexyl)undecanoic acid prepared in Example 14 and sodium methoxide (1.0 mol/l in methanol), a procedure analogous to that as shown in Example 27 was repeated to give sodium 11-[(3RS,4RS)-7-hydroxy-3-(4-hydroxyphenyl)-3-methylchroman-4-yl]-2-(3,3,4,4,5,5,6,6,6-nonafluorohexyl)undecanoate.

$^1$H-NMR(270 MHz, CD$_3$OD): δ 6.98 (d, J=8.6 Hz, 2H), 6.75 (d, J=8.3 Hz, 1H, C5-H), 6.68 (d, J=8.6 Hz, 2H), 6.21 (dd, J=8.3, 2.3 Hz, 1H, C6-H), 6.14 (d, J=2.3 Hz, 1H, C8-H), 4.39 (d, J=10.2 Hz, 1H, C2-H$_2$), 4.09 (d, J=10.2 Hz, 1H, C2-CH$_2$), 2.6–2.5 (m, 1H, C4-H), 2.3–1.9 (m, 3H), 1.8–1.4 (m, 3H), 1.3–0.9 (m, 20H).

Test Example 1

Anti-estrogenic Activity (Oral Administration)

Test compounds were assayed for their oral anti-estrogenic activity in the following manner. In this experiment, the compounds prepared in Examples mentioned above were used as test compounds. As control compounds, the following three were used: a compound described in Example 7 of WO98/25916; ZM; and a compound corresponding to general formula (1) of the present invention, provided that R$_2$ was a C$_2$ perfluoroalkyl group (perfluoroethyl), i.e., 10-[(3RS,4RS)-7-hydroxy-3-(4-hydroxyphenyl)-3-methylthiochroman-4-yl]-2-(4,4,5,5,5-pentafluoropentyl)decanoic acid, which had been synthesized according to Reaction Schemes 1 to 7 mentioned above.

To determine anti-estrogenic activity, mice (ICR, weight 30±2 g) which had been ovariectomized 2 weeks before were subcutaneously administered with 17β-estradiol-benzoate (Sigma) in an amount of 0.1 μg/mouse for 3 days and the degree by which the test compound inhibited the increase in uterine weight was measured. In this experiment, each of the test and control compounds was suspended in 5% arabic gum solution and orally administered for 3 days on a once-a-day basis. After 24 hours from the last administration, the test animals were sacrificed and the uteri were removed and weighed. The results obtained are shown in Table 4 below.

TABLE 4

Anti-estrogenic activity in ovariectomized mice administered with 17β-estradiol (oral administration, 3 days)

| Test compound/dose (p.o., 3 days) | | Inhibition |
|---|---|---|
| Compound | mg/kg | (%) |
| Example 8 | 10 | 93 |
| Example 9 | 10 | 93 |
| Example 11 | 10 | 85 |
| Example 12 | 10 | 86 |
| Example 13 | 10 | 84 |
| Example 14 | 10 | 88 |
| Example 15 | 10 | 92 |
| Example 16 | 10 | 91 |
| Example 21, Peak 1 | 10 | 89 |
| Example 21, Peak 2 | 10 | 96 |
| Example 24, Peak 1 | 10 | 85 |
| Example 21, Peak 2 | 10 | 91 |
| Example 7 of WO98/25916 | 10 | 68 |
| ZM | 10 | 42 |
| 10-[(3RS, 4RS)-7-hydroxy-3-(4-hydroxyphenyl)-3-methyl-thiochroman-4-yl]-2-(4,4,5,5,5-pentafluoropentyl) decanoic acid | 10 | 75 |

The results shown in Table 4 above indicate that the compounds of the present invention show a superior inhibitory activity against the estradiol-induced increase in uterine weight, as compared to the anti-estrogenic compounds: the compound described in Example 7 of WO98/25916, ZM, and 10-[(3RS,4RS)-7-hydroxy-3-(4-hydroxyphenyl)-3-methylthiochroman-4-yl]-2-(4,4,5,5,5-pentafluoropentyl) decanoic acid.

INDUSTRIAL APPLICABILITY

The compounds of the present invention are advantageous in pharmaceutical use because they have an excellent anti-estrogenic activity as well as providing a sufficiently high activity even when administered orally.

What is claimed is:

1. A compound having the following formula (1):

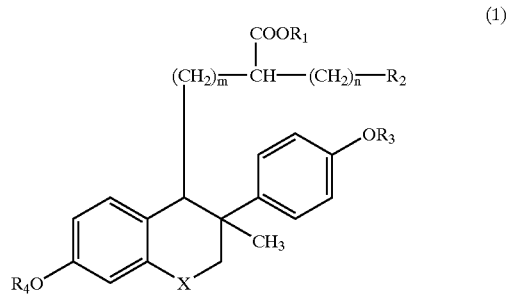

in which

R$_1$ represents a hydrogen atom or a salt-forming metal;

R$_2$ represents a linear or branched C$_3$–C$_5$ perhalogenoalkyl group or a group of the following general formula (2):

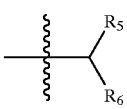

(2)

in which
each of $R_5$ and $R_6$ represents a linear or branched $C_1$–$C_3$ perhalogenoalkyl group;
each of $R_3$ and $R_4$ independently represents a hydrogen atom, an optionally substituted linear or branched $C_1$–$C_3$ alkyl group, an acyl group or a salt-forming metal;
X represents an oxygen atom or a sulfur atom;
m represents an integer of 2 to 14; and
n represents an integer of 0 to 8;
or an enantiomer of the compound, or a hydrate or a pharmaceutically acceptable salt of the compound or its enantiomer.

2. The compound according to claim 1, wherein each of $R_3$ and $R_4$ in formula (1) is independently a hydrogen atom or a salt-forming metal, or an enantiomer of the compound, or a hydrate or a pharmaceutically acceptable salt of the compound or its enantiomer.

3. The compound according to claim 1, wherein $R_2$ in formula (1) is a linear or branched $C_3$–$C_5$ perfluoroalkyl group or a group of the following general formula (2):

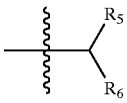

(2)

in which
each of $R_5$ and $R_6$ is a linear or branched $C_1$–$C_3$ perfluoroalkyl group,
or an enantiomer of the compound, or a hydrate or a pharmaceutically acceptable salt of the compound or its enantiomer.

4. The compound according to claim 1, wherein m in formula (1) is an integer of 6 to 10, or an enantiomer of the compound, or a hydrate or a pharmaceutically acceptable salt of the compound or its enantiomer.

5. The compound according to claim 1, wherein n in formula (1) is an integer of 2 to 4, or an enantiomer of the compound, or a hydrate or a pharmaceutically acceptable salt of the compound or its enantiomer.

6. The compound according to claim 1, wherein $R_2$ in formula (1) is a perfluoro-n-butyl group, or an enantiomer of the compound, or a hydrate or a pharmaceutically acceptable salt of the compound or its enantiomer.

7. The compound according to claim 1, wherein in formula (1), $R_1$ is a hydrogen atom, an alkali metal or an alkaline earth metal; $R_2$ is a perfluoro-n-propyl group, a perfluoro-n-butyl group or a 1,1,1,3,3,3-hexafluoroisopropyl group; each of $R_3$ and $R_4$ is independently a hydrogen atom, an alkali metal or an alkaline earth metal; X is an oxygen atom or a sulfur atom; m is an integer of 8 or 9; and n is an integer of 2 to 4; or an enantiomer of the compound, or a hydrate or a pharmaceutically acceptable salt of the compound or its enantiomer.

8. The compound according to claim 1, wherein in formula (1):
a) $R_1$ is a hydrogen atom, $R_2$ is a perfluoro-n-butyl group, $R_3$ is a hydrogen atom, $R_4$ is a hydrogen atom, X is a sulfur atom, m is 8, and n is 2;
b) $R_1$ is a hydrogen atom, $R_2$ is a perfluoro-n-butyl group, $R_3$ is a hydrogen atom, $R_4$ is a hydrogen atom, X is a sulfur atom, m is 8, and n is 3;
c) $R_1$ is a hydrogen atom, $R_2$ is a perfluoro-n-butyl group, $R_3$ is a hydrogen atom, $R_4$ is a hydrogen atom, X is a sulfur atom, m is 8, and n is 4;
d) $R_1$ is a hydrogen atom, $R_2$ is a perfluoro-n-butyl group, $R_3$ is a hydrogen atom, $R_4$ is a hydrogen atom, X is a sulfur atom, m is 9, and n is 2;
e) $R_1$ is a hydrogen atom, $R_2$ is a perfluoro-n-butyl group, $R_3$ is a hydrogen atom, $R_4$ is a hydrogen atom, X is a sulfur atom, m is 9, and n is 3;
f) $R_1$ is a hydrogen atom, $R_2$ is a perfluoro-n-butyl group, $R_3$ is a hydrogen atom, $R_4$ is a hydrogen atom, X is an oxygen atom, m is 8, and n is 2;
g) $R_1$ is a hydrogen atom, $R_2$ is a perfluoro-n-butyl group, $R_3$ is a hydrogen atom, $R_4$ is a hydrogen atom, X is an oxygen atom, m is 9, and n is 2;
h) $R_1$ is a hydrogen atom, $R_2$ is a perfluoro-n-butyl group, $R_3$ is a hydrogen atom, $R_4$ is a hydrogen atom, X is an oxygen atom, m is 8, and n is 3;
i) $R_1$ is a hydrogen atom, $R_2$ is a perfluoro-n-butyl group, $R_3$ is a hydrogen atom, $R_4$ is a hydrogen atom, X is an oxygen atom, m is 9, and n is 3;
j) $R_1$ is a sodium atom, $R_2$ is a perfluoro-n-butyl group, $R_3$ is a hydrogen atom, $R_4$ is a hydrogen atom, X is a sulfur atom, m is 8, and n is 2; or
k) $R_1$ is a sodium atom, $R_2$ is a perfluoro-n-butyl group, $R_3$ is a hydrogen atom, $R_4$ is a hydrogen atom, X is an oxygen atom, m is 9, and n is 2;
or an enantiomer of the compound, or a hydrate or a pharmaceutically acceptable salt of the compound or its enantiomer.

9. The compound according to claim 1, wherein in formula (1), the configuration of 3- and 4-position carbons in the parent scaffold (chroman or thiochroman ring) is (3RS, 4RS), (3R, 4R) or (3S, 4S), or an enantiomer of the compound, or a hydrate or a pharmaceutically accepted salt of the compound or its enantiomer.

10. The compound according to claim 1, wherein in formula (1), the carbon which is on the side chain bonded to the 4-position of the parent scaffold (chroman or thiochroman) and to which the carboxylic acid in said side chain is bonded has R- or S-configuration, or a mixture thereof, or an enantiomer of the compound, or a hydrate or a pharmaceutically acceptable salt of the compound or its enantiomer.

11. The compound according to claim 1, which is selected from the group consisting of:
10-[(3RS,4RS)-7-hydroxy-3-(4-hydroxyphenyl)-3-methylthiochroman-4-yl]-2-(3,3,4,4,5,5,6,6,6-nonafluorohexyl)decanoic acid;
10-[(3RS,4RS)-7-hydroxy-3-(4-hydroxyphenyl)-3-methylthiochroman-4-yl]-2-(4,4,5,5,6,6,7,7,7-nonafluoroheptyl)decanoic acid;
10-[(3RS,4RS)-7-hydroxy-3-(4-hydroxyphenyl)-3-methylthiochroman-4-yl]-2-(5,5,6,6,7,7,8,8,8-nonafluorooctyl)decanoic acid;
11-[(3RS,4RS)-7-hydroxy-3-(4-hydroxyphenyl)-3-methylthiochroman-4-yl]-2-(3,3,4,4,5,5,6,6,6-nonafluorohexyl)undecanoic acid;
11-[(3RS,4RS)-7-hydroxy-3-(4-hydroxyphenyl)-3-methylthiochroman-4-yl]-2-(4,4,5,5,6,6,7,7,7-nonafluoroheptyl)undecanoic acid;
10-[(3RS,4RS)-7-hydroxy-3-(4-hydroxyphenyl)-3-methylchroman-4-yl]-2-(3,3,4,4,5,5,6,6,6-nonafluorohexyl)decanoic acid;

11-[(3RS,4RS)-7-hydroxy-3-(4-hydroxyphenyl)-3-methylchroman-4-yl]-2-(3,3,4,4,5,5,6,6,6-nonafluorohexyl)undecanoic acid;

10-[(3RS,4RS)-7-hydroxy-3-(4-hydroxyphenyl)-3-methylchroman-4-yl]-2-(4,4,5,5,6,6,7,7,7-nonafluoroheptyl)decanoic acid;

11-[(3RS,4RS)-7-hydroxy-3-(4-hydroxyphenyl)-3-methylchroman-4-yl]-2-(4,4,5,5,6,6,7,7,7-nonafluoroheptyl)undecanoic acid;

sodium 10-[(3RS,4RS)-7-hydroxy-3-(4-hydroxyphenyl)-3-methylthiochroman-4-yl]-2-(3,3,4,4,5,5,6,6,6-nonafluorohexyl)decanoate; and sodium 11-[(3RS,4RS)-7-hydroxy-3-(4-hydroxyphenyl)-3-methylchroman-4-yl]-2-(3,3,4,4,5,5,6,6,6-nonafluorohexyl)undecanoate;

or an enantiomer of the compound, or a hydrate or a pharmaceutically acceptable salt of the compound or its enantiomer.

12. A compound represented by Peak 1 or 2 shown in the following formula:

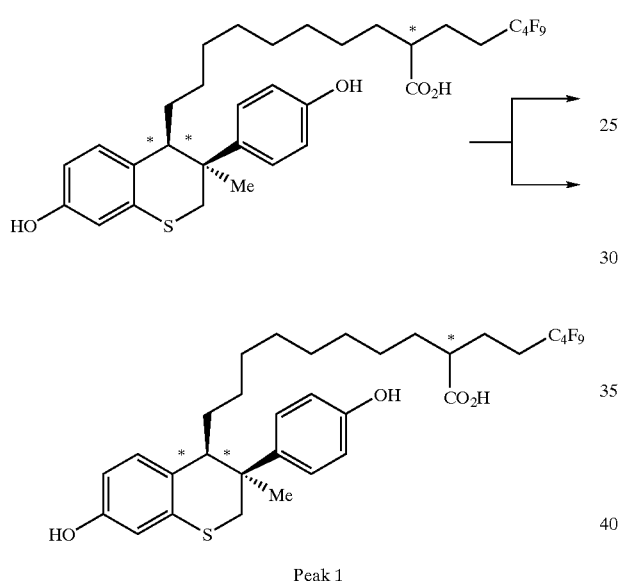

wherein said Peaks 1 and 2 are detected at retention times of 32 and 38 minutes, respectively, when optically resolved and measured under the following conditions:
Column used: CHIRALPAK AD (0.46 cm ID×25 cm L)
Mobile phase: hexane/isopropanol/acetic acid=90/10/0.2 (v/v/v)
Flow rate: 1.0 ml/min
Column temperature: 40° C.
Detection wavelength: 280 nm.

13. A compound represented by Peak 1 or 2 shown in the following formula:

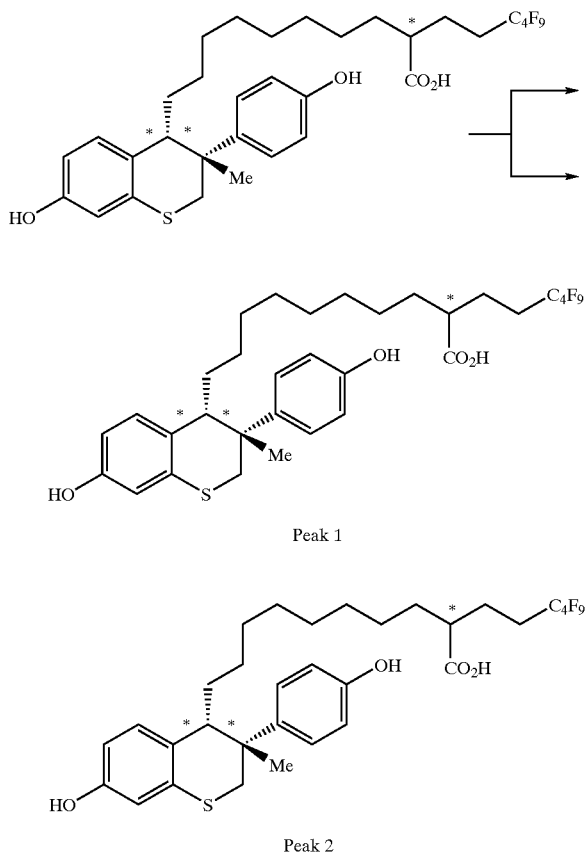

wherein said Peaks 1 and 2 are detected at retention times of 30 and 34 minutes, respectively, when optically resolved and measured under the following conditions:

Column used: CHIRALPAK AD (0.46 cm ID×25 cm L)
Mobile phase: hexane/isopropanol/acetic acid=90/10/0.2 (v/v/v)
Flow rate: 0.8 ml/min
Column temperature: 40° C.
Detection wavelength: 280 nm.

14. A compound represented by Peak 1 or 2 shown in the following formula:

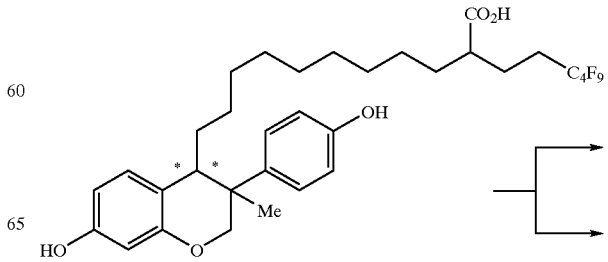

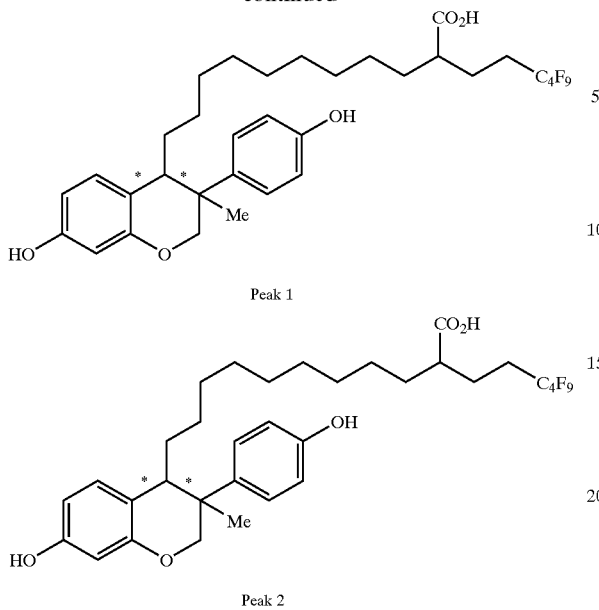

Peak 1

Peak 2 wherein said Peaks 1 and 2 are detected at retention times of 17.5 and 20.7 minutes, respectively, when optically resolved and measured under the following conditions:

Column used: CHIRALPAK AD (0.46 cm ID×25 cm L)

Mobile phase: hexane/isopropanol/acetic acid=90/10/0.1 (v/v/v)

Flow rate: 1.0 ml/min

Column temperature: 40° C.

Detection wavelength: 254 nm.

15. A compound represented by Peak 1 or 2 shown in the following formula:

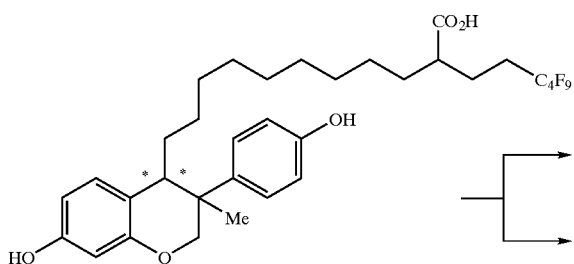

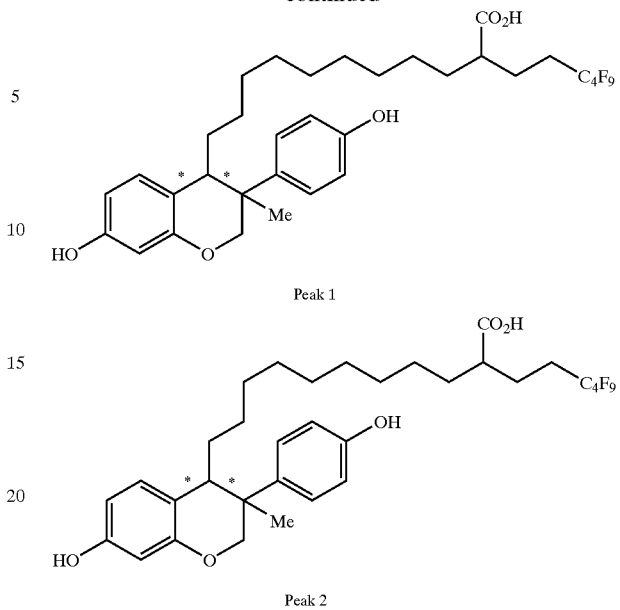

Peak 1

Peak 2 wherein said Peaks 1 and 2 are detected at retention times of 8.4 and 10.8 minutes, respectively, when optically resolved and measured under the following conditions:

Column used: CHIRALPAK AD (0.46 cm ID×25 cm L)

Mobile phase: hexane/isopropanol/acetic acid=80/20/0.1 (v/v/v)

Flow rate: 1.0 ml/min

Column temperature: 40° C.

Detection wavelength: 254 nm.

16. A pharmaceutical composition comprising as an active ingredient, at least one compound according to any one of claims 1 to 15 or enantiomer thereof, or at least one hydrate or pharmaceutically acceptable salt of the compound or its enantiomer.

17. An anti-estrogenic pharmaceutical composition comprising as an active ingredient, at least one compound according to any one of claims 1 to 15 or enantiomer thereof, or at least one hydrate or pharmaceutically acceptable salt of the compound or its enantiomer.

18. A therapeutic agent for breast cancer comprising as an active ingredient, at least one compound according to any one of claims 1 to 15 or enantiomer thereof, or at least one hydrate or pharmaceutically acceptable salt of the compound or its enantiomer.

* * * * *